(12) United States Patent
Kadonaga et al.

(10) Patent No.: US 7,968,698 B2
(45) Date of Patent: Jun. 28, 2011

(54) OPTIMIZED CORE PROMOTERS AND USES THEREOF

(75) Inventors: James T. Kadonaga, Del Mar, CA (US); Tamar Gershon, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 678 days.

(21) Appl. No.: 11/920,986

(22) PCT Filed: May 25, 2006

(86) PCT No.: PCT/US2006/020394
§ 371 (c)(1), (2), (4) Date: Nov. 23, 2007

(87) PCT Pub. No.: WO2006/127980
PCT Pub. Date: Nov. 30, 2006

(65) Prior Publication Data
US 2010/0129863 A1    May 27, 2010

Related U.S. Application Data

(60) Provisional application No. 60/684,482, filed on May 25, 2005.

(51) Int. Cl.
*C07H 21/04* (2006.01)

(52) U.S. Cl. .................. 536/24.1; 435/69.1; 435/320.1; 424/93.21

(58) Field of Classification Search .................. None
See application file for complete search history.

(56) References Cited

U.S. PATENT DOCUMENTS 5,518,913 A * 5/1996 Massie et al. .............. 435/235.1
6,124,094 A * 9/2000 Lajoie et al. ..................... 435/6

OTHER PUBLICATIONS

Kutach et al. Mole Cell Biol 2000;20:4754.*
Lim, C. Y. et al. *The MTE, a new Core Promoter Element for Transcription by RNA Polymerase II: Genes & Development*, 2004, vol. 18, pp. 1606-1617.

* cited by examiner

*Primary Examiner* — Q. Janice Li
(74) *Attorney, Agent, or Firm* — Benjamin Aaron Adler

(57) ABSTRACT

The present invention provides core promoter motif ten elements (MTE) and core promoter constructs comprising the MTEs and an initiator element (Inr) in combination with one or both of a TATA box and a downstream promoter element (DPE) which increases gene expression over the strongest known core promoters. Particularly, an optimized or super core promoter is provided which comprises Inr, MTE, TATA box and DPE elements. The present invention also provides expression vectors and host cells comprising the core promoter constructs. Additionally, methods of increasing production of a protein using the core promoter constructs are provided.

34 Claims, 19 Drawing Sheets

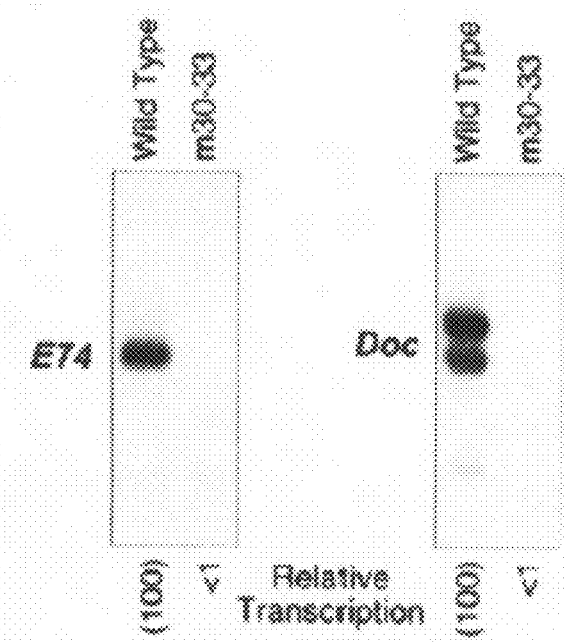
Fig. 4A
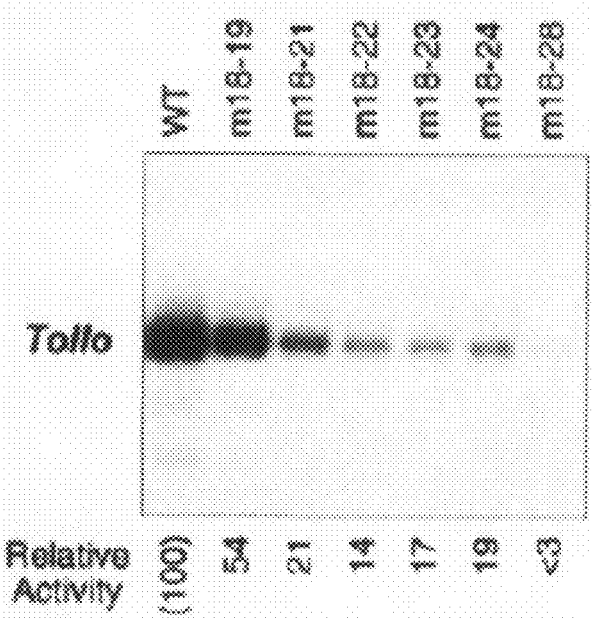
Fig. 4B
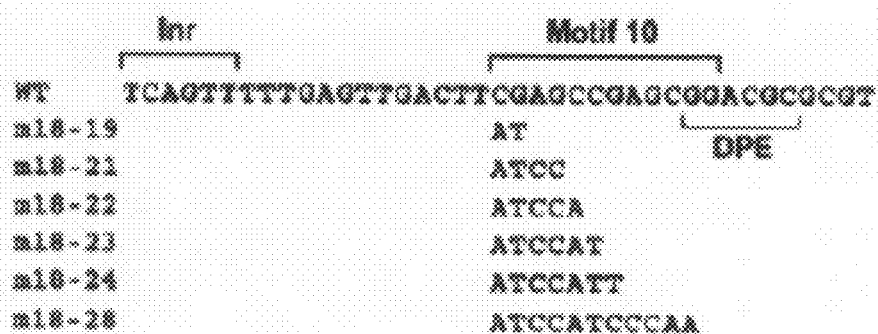
SEQ ID NOS: 43-49

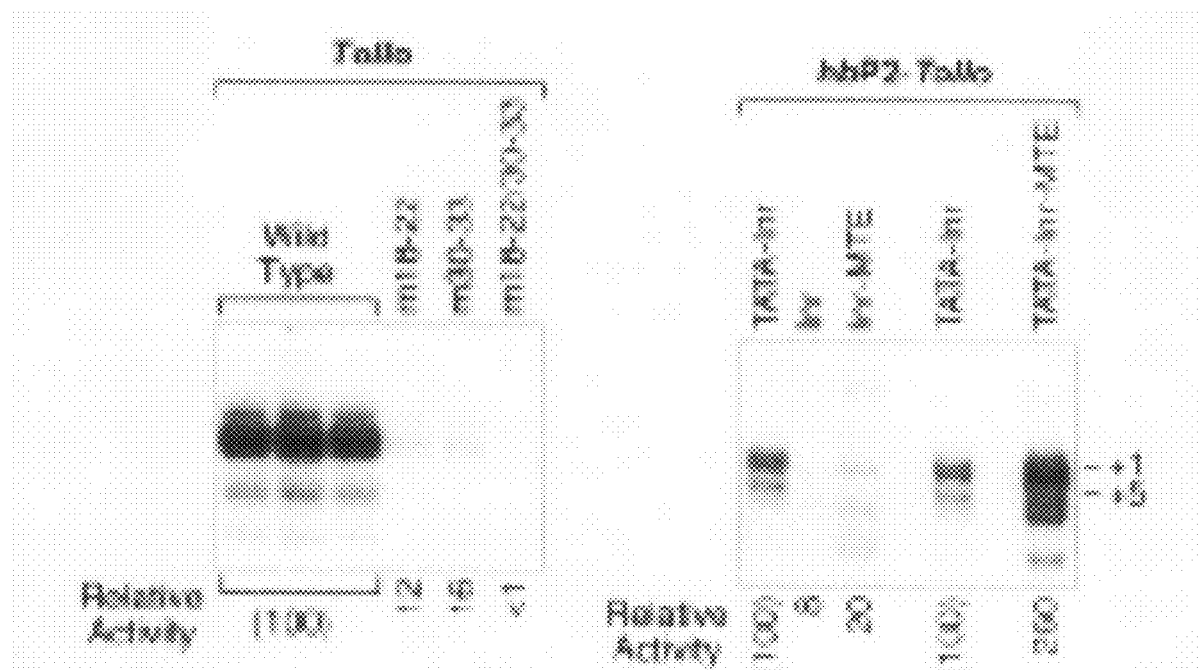
Fig. 10A
Fig. 10C
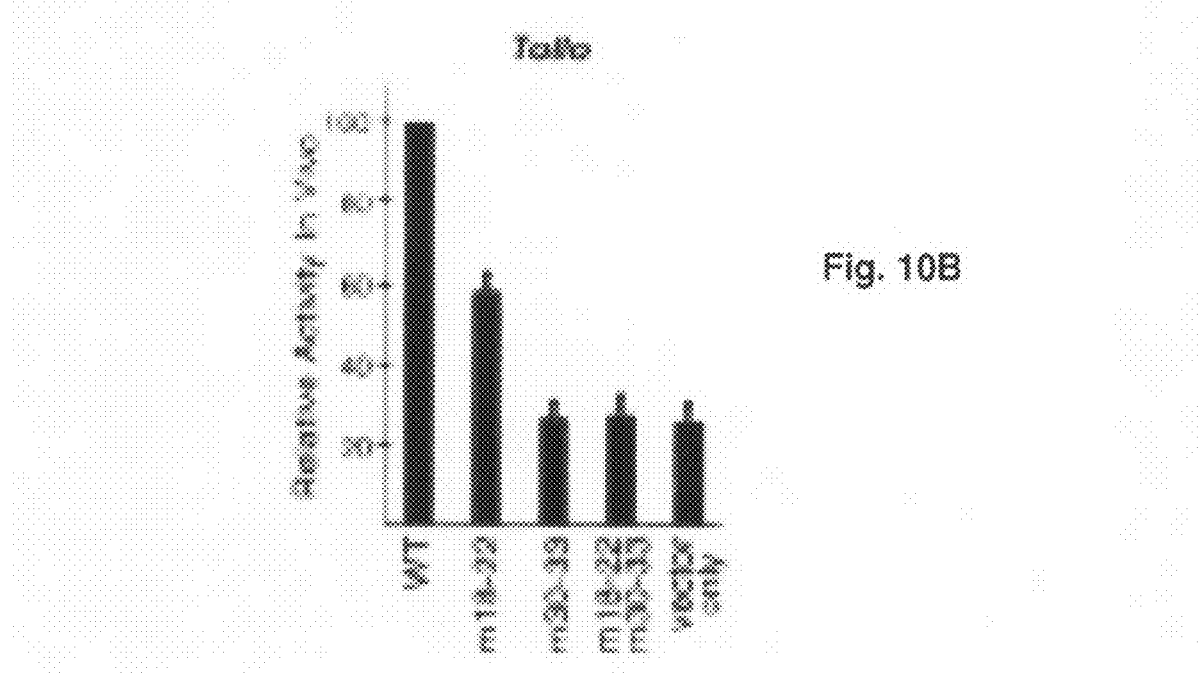
Fig. 10B

OPTIMIZED CORE PROMOTERS AND USES THEREOF

CROSS-REFERENCE TO RELATED APPLICATIONS

This U.S. national stage application is filed under 35 U.S.C. §363 and claims benefit of priority under 35 U.S.C. §365 of international application PCT/US2006/020394, filed May 25, 2006, which claims benefit of priority under 35 U.S.C. §119(e) of provisional U.S. Ser. No. 60/684,482, filed May 25, 2005.

FEDERAL FUNDING LEGEND

This invention was produced in part using funds obtained through grant R01-GM041249 from the National Institutes of Health. Consequently, the federal government has certain rights in this invention.

BACKGROUND OF THE INVENTION

1. Field of the Invention

The present invention relates generally to the fields of molecular biology and protein chemistry of promoters. More specifically, the present invention relates to optimized core promoters, the design thereof and uses therefor.

2. Description of the Related Art

The regulation of gene expression at the level of transcription is a key control point for many cellular processes. In eukaryotes, there are tens of thousands of protein-coding genes, each of which has its own unique program of transcription. To understand how these transcriptional programs are encoded in the DNA template, it is necessary to understand the fundamental molecular mechanisms by which transcription is regulated.

Transcription by RNA polymerase II involves a network of factors that include sequence-specific DNA-binding proteins, transcriptional coregulators, chromatin remodeling factors, enzymes that covalently modify histones (and other proteins), and the basal transcriptional machinery. A proportion of the regulatory information that specifies the transcriptional program of each gene is encoded in promoters and enhancers. However, the ultimate target sequence of the vast array of factors that control the initiation of transcription is the core promoter (1-5).

The core promoter encompasses the RNA start site and directs the accurate initiation of transcription. Core promoters are typically about 50 nt in length, and consist of functional subregions termed core promoter elements. These core promoter elements are not universally present in all core promoters. Rather, core promoter elements confer the specific properties of each core promoter, such as the interactions of core promoters with enhancer elements. Some of these core promoter motifs are as follows.

The TATA box (6) is an A/T-rich sequence that is located approximately 26 to 31 nt upstream of the transcription start site. The TATA box is a recognition site for the binding of the TATA box-binding protein (TBP) subunit of TFIID. The TFIIB recognition element (BRE) is located immediately upstream of about 12% of TATA boxes (7). The initiator element (Inr) encompasses the transcription start site (8). The Inr is recognized by the TAF1 (TAFII250) and TAF2 (TAFII150) subunits of the TFIID complex (see, e.g., 9-12) as well as several other factors (discussed in 5).

The DPE is a downstream core promoter element that is located from +28 to +33 relative to the A+1 in the Inr motif (13-15). A typical DPE-dependent promoter has Inr and DPE motifs and lacks a TATA box. The spacing between the Inr and DPE motifs has been observed to be identical in all (~30) DPE-dependent promoters examined thus far. The DPE is conserved from *Drosophila* to humans, and appears to be as common as the TATA box in *Drosophila* core promoters. TFIID binds cooperatively to the Inr and DPE motifs (13). Photocrosslinking analyses indicated that the TAF6 (TAF60) and TAF9 (TAF40) subunits of *Drosophila* TFIID are in close proximity to the DPE (14). Gel shift analyses further revealed sequence-specific binding of TAF6-TAF9 complexes to the DPE motif (16). In addition, TAF9 in vivo associates preferentially with the DPE-containing human IRF-1 promoter relative to a DPE-mutant version of the promoter (17).

There are significant differences in the mechanisms of transcription from DPE- versus TATA-dependent core promoters. For instance, NC2 (negative cofactor 2; also known as Dr1-Drap1), which had been initially identified as a repressor of transcription from TATA-containing promoters, was an activator of basal transcription from DPE-dependent core promoters (18). In addition, some enhancers activate transcription from DPE-dependent core promoters but not from TATA-dependent core promoters, and vice versa (19). Thus, the core promoter is a regulatory element that is an important component of enhancer function. The differences between DPE- versus TATA-directed transcription are further revealed by the analysis of the factors that are required for basal transcription. With TATA-dependent promoters, accurate initiation of transcription is mediated by RNA polymerase II along with the basal ('general') factors—TFIIA, TFIIB, TFIID, TFIIE, TFIIF, and TFIIH. In contrast, transcription of DPE-dependent promoters does not occur with the same highly purified basal transcription factors in the presence or absence of purified recombinant dNC2.

Most scientists have attempted to enhance gene expression by optimization and/or modification of the elements that are bound by sequence-specific DNA-binding proteins that interact with proximal promoter and enhancer elements, which is useful and successful. However, the core promoter has been overlooked in such endeavors, largely because of a general lack of knowledge and appreciation of the core promoter. The synthesis of recombinant proteins has been widely employed in the biotech industry for the production of important pharmaceuticals such as insulin, human growth hormone, erythropoietin (EPO), and tissue plasminogen activator (tPA). Some proteins, such as insulin, are produced in bacteria while other proteins, e.g., EPO and tPA, are produced in metazoan cells (that is, multicellular animal cells, which include mammalian and insect cells) to achieve the posttranslational processing that is necessary for biological activity. The present invention is relevant to the latter category of recombinant proteins that are produced in metazoan cells.

There is a need in the art for improved production of recombinant proteins by focusing on the core promoter element, instead of upstream promoter and enhancer elements. Specifically, the prior art is deficient in optimized core promoters useful in methods of increasing protein production in metazoan cells. The present invention fulfills this long-standing need and desire in the art.

SUMMARY OF THE INVENTION

The present invention is directed to a synthetic core promoter element comprising a nucleic acid sequence derived from a consensus sequence shown in SEQ ID NO: 2.

The present invention also is directed to a core promoter construct comprising a nucleic acid sequence of a core promoter initiator element (Inr) and a nucleic acid sequence of a core promoter motif ten element (MTE) operably positioned therewith. The present invention is directed to a related core promoter construct further comprising a nucleic acid sequence linking the Inr and the MTE where the nucleic acid sequence has a non-negative effect on core promoter function. The present invention is directed to another related core promoter construct further comprising a nucleic acid sequence of a TATA box or a nucleic acid sequence of a downstream promoter element (DPE) or a combination thereof. The present invention also is directed to yet another related core promoter construct further comprising nucleic acid sequences linking Inr, MTE, TATA box and DPE in an operable position within the construct such that the nucleic acid sequences have a non-negative effect on core promoter function.

The present invention is directed further to another core promoter construct. The construct comprises a nucleic acid sequence of a core promoter initiator element (Inr), a nucleic acid sequence of a core promoter motif ten element (MTE), a nucleic acid sequence of a TATA box, a nucleic acid sequence of a downstream promoter element (DPE), and other nucleic acid sequences linking Inr, MTE, TATA box and DPE in a synergistically operable position within the construct. The other nucleic acid sequences have a non-negative effect on core promoter function.

The present invention is directed further still to a Super Core Promoter having the sequence shown in SEQ ID NO: 8, SEQ ID NO: 23, SEQ ID NO: 59, SEQ ID NO: 60 or SEQ ID NO: 61.

The present invention is directed further still to expression vectors comprising the core promoter constructs and Super Core Promoter described herein. The present invention also is directed to metazoan host cells comprising the expression vectors described herein. The present invention is directed further still to kits comprising the core promoter constructs and Super Core Promoter described herein. The present invention also is directed to a related kit further comprising expression vectors comprising the core promoter constructs and Super Core Promoter described herein and metazoan host cells suitable to comprise and express the expression vectors.

The present invention is directed further still to a method of increasing production of a protein. The methods comprise introducing into a metazoan host cell an expression vector comprising the core promoter constructs or Super Core Promoter described herein and a nucleic acid sequence encoding a protein. The metazoan host cells are cultured under conditions suitable to express the protein and the expressed protein is isolated. The core promoters or the Super Core Promoters increase expression of the nucleic acid sequence encoding the protein thereby increasing production thereof.

The present invention is directed further still to a method for increasing the expression of genes in a metazoan animal. The method comprises introducing an expression vector comprising the core promoter construct described herein and a nucleic acid sequence comprising one or more genes into a metazoan animal such that a transgenic metazoan animal is formed. The core promoter increases expression of the gene(s) comprising the expression vector therein. The present invention is directed further still to a method of designing an optimized core promoter to increase transcription of a gene. The method comprises selecting a nucleic acid sequence for a core promoter initiator element (Inr) and for a core promoter motif ten element (MTE) and selecting a nucleic acid sequence for one or more other core promoter elements. A level of transcriptional activity of Inr operably linked to MTE is compared with a level of transcriptional activity of operably linked Inr, MTE and one or more of the other core promoter elements. A combination of Inr, MTE and the one or more other core promoter elements that has the highest level of transcriptional activity is the optimized core promoter.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 2A shows putative core promoters that contained a motif 10 consensus sequence that were identified in the *Drosophila* genome database by using the JDSA search program. In these putative core promoters, the motif 10 consensus was located from +18 to +29 relative to the $A_{+1}$ position in the initiator (Inr) consensus sequence. FIG. 2B identifies five motif 10-containing core promoters. The in vivo start sites were mapped by primer extension analysis with poly(A)$^+$ RNA (15 µg) from *Drosophila* embryos that were collected from 0 to 12 h after egg deposition. The in vitro start sites were mapped with RNA that was synthesized in vitro with a nuclear extract derived from *Drosophila* embryos. Where indicated, α-amanitin (α-am, 4 µg/mL) was included in the in vitro transcription reactions. For each promoter, the primer extension products were subjected to denaturing polyacrylamide gel electrophoresis in parallel with DNA sequencing ladders that were generated from the same primers that were used in the primer extension analyses of the RNA. Transcription from each of these promoters appeared to start from the C nucleotide that was immediately upstream of the $A_{+1}$, which will be referred to as +1 position of the Inr consensus sequence.

FIG. 4A-4B show non-overlapping mutations in the motif 10 sequence and the DPE. FIG. 4A shows that the +30-33 DPE mutation inactivates DPE-dependent promoters. The +30 to +33 region of the E74B and Doc core promoters were mutated to CATA (SEQ ID NO: 12). The resulting m30-33 promoters were subjected to in vitro transcriptional analysis in parallel with the corresponding wild-type promoters. FIG. 4B shows the results of analysis of mutations in the motif 10 sequence (+19 to +29) that did not overlap with the DPE (+28 to +33). A series of progressive substitution mutant versions of the Tollo core promoter were constructed as depicted at the bottom of the figure. The substitution mutations were chosen to minimize the similarity of the sequences of the motif 10 consensus. The wild type and the mutant promoters were subjected to in vitro transcription analysis with a *Drosophila* nuclear extract.

FIG. 5A shows that MTE and DPE motifs both contributed to transcription from the Tollo, CG10479 and CG15695 core promoters. The wild type, m18-22, m30-33 and m18-22/30-33 versions of each core promoter were subjected to in vitro transcription analysis with *Drosophila* nuclear extract. FIG. 5B shows that the E74B and Doc core promoters lacked a functional MTE that could support transcription upon mutation of the DPE. Wild type and mutant promoters were analyzed as in 5A.

FIG. 6A shows that the Inr was required for transcription from MTE-containing promoters. In the mutant Inr (mInr) promoters, the Inr sequences (FIG. 2) were mutated to GTGACA (SEQ ID NO: 13). The constructs were subjected to in vitro transcription analysis with a *Drosophila* nuclear extract. FIG. 6B shows that the spacing between the Inr and the MTE was important for core promoter activity. A series of mutant promoters were constructed in which the spacing between the Inr and MTE was either increased or decreased by one or three nucleotides. To ensure that the effects were due to interactions between the Inr and MTE, all of the promoters contained the m30-33 mutation (CATA at +30-33; SEQ ID NO: 12) that inactivated the DPE motif. The constructs were subjected to in vitro transcription analysis with a *Drosophila* nuclear extract. The transcriptional activity of each mutant promoter was reported relative to that of the m30-33 promoter with wild type spacing (0) between the Inr and the MTE.

FIGS. 10A-10E show that human transcription factors recognize the MTE. FIG. 10A shows that the MTE in the *Drosophila* Tollo core promoter was recognized by human basal transcription factors. The Tollo promoter constructs described in FIG. 5 were transcribed with a HeLa nuclear extract. FIG. 10B shows transient transfection analysis of wild-type and mutant Tollo core promoters in HeLa cells. The wild type, m18-22, m30-33 and m18-22/30-33 versions of the Tollo-luc reporter constructs as well as the promoterless vector (pGL3-Basic, "vector only") were transiently transfected in HeLa cells and the relative activities were determined. FIG. 10C shows that the MTE exhibits synergy with the TATA-box as well as weak activity in the absence of the TATA and DPE motifs with human transcription factors. The hbP2-Tollo hybrid promoter constructs shown in FIG. 8 were transcribed with a HeLa nuclear extract. FIG. 10D shows that the MTE could compensate for the loss of the DPE and exhibited synergy with the DPE with human transcription factors. The E74B-based constructs shown in FIG. 7 were transcribed with a HeLa nuclear extract. FIG. 10E shows that the human sterol C5 desaturase-like (SC5DL) gene has an MTE-dependent promoter. The wild type, m18-22, m30-33 and m18-22/30-33 versions of the SC5DL promoter were subjected to in vitro transcription analysis with a HeLa nuclear extract.

FIG. 12C shows the rate of formation of the preinitiation complex (PIC) formation. PIC assembly was allowed to occur for a variable time t in the absence of ribonucleoside 5'-triphosphate (rNTPs). Sarkosyl (0.2%, w/v, final concentration) was then added to inhibit transcription reinitiation but not elongation.

FIG. 14B shows that each individual element is important for the enhanced activity of the SCP.

FIG. 18A shows the SCP2 activity in HeLa S3 cells. The four pRC/CMV-based constructs and pGL3-Control (as a reference) were transfected into HeLa S3 cells. All transfections also included a β-galactosidase expression plasmid as a control for transfection efficiency. The resulting luciferase activities were normalized to the corresponding β-galactosidase activities. The values reported are relative to the pGL3-Control and are derived from three independent experiments in which each condition was performed in quadruplicate. FIG. 18B shows the SCP2 activity in CHO cells. CHO cells were transfected with pRC/CMV-based plasmids containing the natural CMV core promoter (CMV) or SCP2 with a luciferase reporter gene, as described above. A β-galactosidase expression plasmid was also cotransfected as a reference. The luciferase activity of each sample was normalized to its corresponding β-galactosidase activity. Each reported value is the average of triplicate samples.

DETAILED DESCRIPTION OF THE INVENTION

Figures 1, 2A:
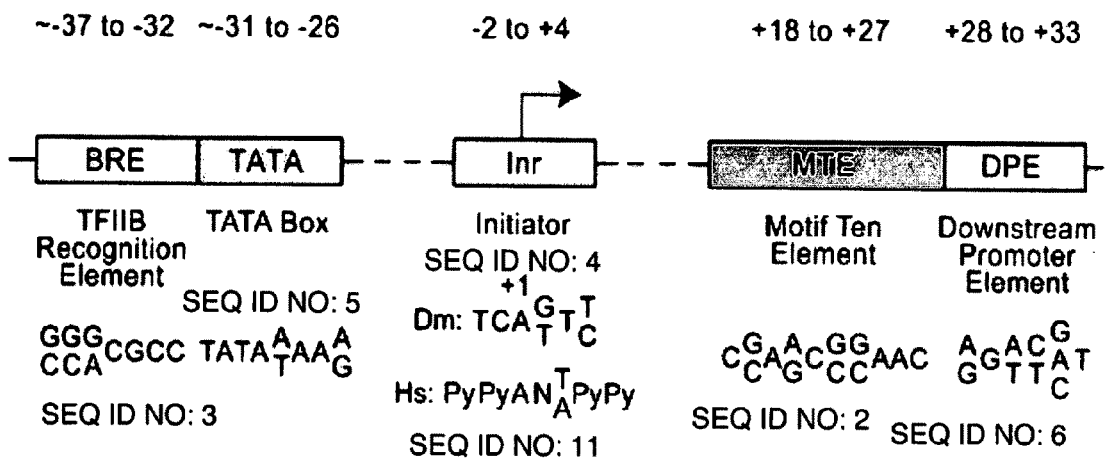
FIG. 1 shows some core promoter motifs that could participate in transcription by RNA polymerase II. Each of these elements was found in only a subset of core promoters. Any specific core promoter may contain some, all or none of these motifs. The DPE consensus was determined with *Drosophila*. The Inr consensus was shown for *Drosophila* (DM) and humans (hs).
FIGS. 2A-2B identify some core promoters that contained a motif 10 sequence.

In one embodiment of the present invention there is provided a synthetic core promoter element comprising a nucleic acid sequence derived from a consensus sequence shown in SEQ ID NO: 2.

In another embodiment of the present invention there is provided a core promoter construct, comprising a nucleic acid sequence of a core promoter initiator element (Inr); and a nucleic acid sequence of a core promoter motif ten element (MTE) operably positioned therewith. Further to this embodiment the core promoter construct may comprise a nucleic acid sequence linking the Inr and the MTE, the nucleic acid sequence having a non-negative effect on core promoter function. In all aspects of this further embodiment the linking nucleic acid sequence may comprise another core promoter sequence. The linking nucleic acid sequence may be a *Drosophila* G element core promoter sequence.

In another further embodiment the core promoter construct may comprise a nucleic acid sequence of a TATA box; or a nucleic acid sequence of a downstream promoter element (DPE); or a combination thereof. Further yet the core promoter construct may comprise nucleic acid sequences linking Inr, MTE, TATA box and DPE in an operable position within the construct, the nucleic acid sequences having a non-negative effect on core promoter function. In yet another further embodiment, the core promoter construct may comprise all of a nucleic acid sequence of a core promoter initiator element (Inr); a nucleic acid sequence of a core promoter motif ten element (MTE); a nucleic acid sequence of a TATA box; a nucleic acid sequence of a downstream promoter element (DPE); and other nucleic acid sequences linking Inr, MTE, TATA box and DPE in a synergistically operable position within the construct, where the other nucleic acid sequences have a non-negative effect on core promoter function.

In aspects of these further embodiments the linking nucleic acid sequences may comprise other core promoter sequences or a consensus of sequences found in the same relative positions to the transcription start site in a metazoan core promoter. The linking nucleic acid sequences may comprise one or more sequences from CMV core promoter, AdML core promoter, *Drosophila* Kruppel (Kr) core promoter, *Drosophila* Tollo core promoter (Tollo), or *Drosophila* G element (G) core promoter. Representative examples of core promoter constructs are SEQ ID NOS: 8, 23, 59, 60, or 61.

In all aspects of these further embodiments, the TATA box sequence may be derived from a consensus sequence shown in SEQ ID NO: 5 or derived from the CMV TATA sequence. Also, in all aspects the DPE sequence may be derived from a consensus sequence shown in SEQ ID NO: 6. In all aspects of any of these embodiments the Inr sequence may be derived from a consensus sequence shown in SEQ ID NO: 4 or derived from the CMV Inr sequence. Also, in all aspects of these embodiments the MTE sequence maybe derived from a consensus sequence shown in SEQ ID NO: 2. In a related embodiment there are provided Super Core Promoters having the sequence shown in SEQ ID NO: 8, 23 59, 60, or 61.

In a another embodiment the present invention provides an expression vector comprising the core promoter construct as described supra. Further to this embodiment the expression vector may comprise a nucleic acid encoding a therapeutic protein, a reporter protein, a transcription enhancer element or a combination thereof operably linked to the promoter. Examples of a therapeutic protein are erythropoietin, tissue plasminogen activator or an antibody. Examples of a reporter protein are β-galactosidase, a luciferase, chloramphenicol acetyl transferase and green fluorescent protein. An example of a transcription enhancer element used in expression vectors is the SV40 enhancer element. The core promoter construct can also be used in viral expression vectors known to those having ordinary skill in this art such as lentivirus expression systems.

In a related embodiment there is provided a metazoan host cell comprising and expressing the expression vector as described supra. Examples of metazoan host cells are HeLa cells and Chinese hamster ovary (CHO) cells, baby hamster kidney cells (BHK), human embryonic kidney cells (HEK-293), or *Drosophila* S2 cells. In yet another embodiment of the present invention there is provided a kit comprising the core promoter construct, as described supra. Further to this related embodiment the kit may comprise an expression vector comprising the core promoter construct and a metazoan host cell suitable to express said expression vector. The expression vector and metazoan host cell are as described supra.

In yet another embodiment of the present invention there is provided a method of increasing production of a protein in a metazoan cell, comprising introducing into a metazoan host cell an expression vector comprising the core promoter construct described supra and a nucleic acid sequence encoding a protein; culturing the metazoan host cell under conditions suitable to express the protein; and isolating the expressed protein, where the core promoter increases expression of the nucleic acid sequence encoding the protein thereby increasing production thereof. In all aspects of this embodiment the nucleic acid sequence may encode a therapeutic protein, a reporter protein or a combination thereof. The therapeutic protein and the reporter protein are as described supra. In a related embodiment there is provided a method for increasing expression of genes in a metazoan animal, comprising introducing an expression vector comprising the core promoter construct described supra and a nucleic acid sequence comprising one or more genes into a metazoan animal such that a transgenic metazoan animal is formed, where the core promoter increases expression of the gene(s) comprising the expression vector therein. Examples of a metazoan animal are *Drosophila*, a leech, a mouse, or a human.

In yet another embodiment of the present invention there is provided a method of designing an optimized core promoter to increase transcription of a gene, comprising selecting a nucleic acid sequence for a core promoter initiator element (Inr) and for a core promoter motif ten element (MTE); selecting a nucleic acid sequence from sequences comprising one or more other core promoters; comparing a level of transcriptional activity of Inr operably linked to MTE with a level of transcriptional activity of operably linked Inr, MTE and one or more of the other core promoter elements; where a combination of Inr, MTE and one or more other core promoter elements having the highest level of transcriptional activity is the optimized core promoter.

In all aspects of this embodiment the Inr sequence may be derived from a consensus sequence shown in SEQ ID NO: 4 or derived from the CMV Inr sequence. Also, in all aspects the MTE sequence is derived from a consensus sequence shown in SEQ ID NO: 2. Furthermore, in all aspects the one or more other core promoter sequences may comprise a TATA box sequence or a DPE sequence, or a *Drosophila* G element core promoter sequence, a *Drosophila* Tollo core promoter sequence, a *Drosophila* Krüppel core sequence, a CMV core promoter sequence, or an AdML core promoter sequence or a combination thereof. Particular to these aspects the TATA box sequence may be derived from a consensus sequence shown in SEQ ID NO: 5 or derived from the CMV TATA sequence. Also, the DPE sequence may be derived from a consensus sequence shown in SEQ ID NO: 6. Examples of optimized core promoters are as shown in SEQ ID NOS: 8, 23 59, 60, or 61.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. As used herein, the term, "enhancer element" refers to DNA sequences that bind transcription factors (enhancer-binding proteins) and thereby enhance the rate of transcription. Examples of enhancer elements used in expression vectors to enhance transcription are the CMV enhancer element and the SV40 enhancer element.

The present invention provides a system in which significantly higher levels of transcription by RNA polymerase II was achieved in eukaryotes, including mammals and insects, by the design and use of an optimized core promoter element. It is contemplated that the incorporation of an optimized core promoter into currently-used expression vectors will enhance the levels of production of a wide variety of proteins in metazoan cells. The present invention also identifies, designs, optimizes and characterizes a novel core promoter motif ten element (MTE) and core promoters comprising at least an initiator element (Inr) and the MTE element described herein. Furthermore, by demonstrating this core promoter to be stronger than previously known strong core promoters, the present invention provides an improvement over the existing knowledge in metazoan gene expression vectors, which includes both cellular and viral (such as lentiviral) expression systems.

Motif 10 was initially identified as a downstream, over-represented sequence of unknown function in a computational analysis of *Drosophila* core promoters (20). Motif 10 has a consensus sequence CSARCSSAACGS (SEQ ID NO: 1) and contains the MTE CSARCSSAAC (SEQ ID NO: 2). MTE is a distinct downstream core promoter sequence motif that functions with other motifs within the core promoter. Nine other motifs have been identified within the core promoter encompassing a region from −60 to +40 relative to the transcription start site of which Motifs 2-4 and 9 are known to comprise elements contributing to core promoter function. Motif 2 comprises the DNA replication-related element (DRE), Motif 4 comprises the initiator element (Inr) TCAKTY (SEQ ID NO: 4) with A+1, Motif 3 comprises the TATA Box TATAWAAR (SEQ ID NO: 5) and Motif 9 comprises the downstream promoter element (DPE) RGWYVT (SEQ ID NO: 6) (FIG. 1). It is contemplated that the remaining motifs 1 and 5-8 are assessed for function within the core promoter.

Particularly, MTE functions with Inr to promote transcription. The spacing between the MTE and the Inr is important for the activity of the core promoter. The MTE promoted transcription of a gene when it was located +18 to +27 nucleotides relative to A+1 position in the Initiator element where nucleotides from +18 to +22 are required for MTE-dependent transcription. MTE functions independently or synergistically with the TATA box or Downstream Promoter Element (DPE). MTE is conserved from *Drosophila* to humans.

As such, provided herein are MTE sequences comprising and/or optimized from the consensus sequence CSARCS-SAAC (SEQ ID NO: 2) to increase gene transcription. It is contemplated that an optimized sequence may comprise a further nucleotide at position +17 or may replace a nucleotide at one or more positions +23 to +27 as long as such additions or substitutions have at least a non-negative effect on transcription as determined by in vitro gene transcription assays known in the art. For example, a preferred optimized MTE sequence is from the *Drosophila* Tollo core promoter located at +17 to +27 with sequence TCGAGCCGAGC (SEQ ID NO: 7).

Additionally, the present invention provides core promoter constructs comprising an Inr sequence and a MTE sequence operably positioned within the core promoter to increase gene transcription and thereby protein production. The core promoters further may comprise one or both of a TATA Box sequence and a DPE sequence. Addition of these sequences further strengthens the core promoter and enhances gene transcription synergistically. Furthermore, the core promoter may comprise additional nucleic acid sequences having at least a non-negative effect on transcription from other strong core promoters, such as, but not limited to, *Drosophila*, human, CMV, or AdML core promoters.

The sequences selected for any component elements of the core promoter may be optimized to yield maximum gene transcription. Optimized elements have nucleic acid sequences designed to operate synergistically within the promoter when properly positioned therein. Potential sequences may be derived from consensus sequences or other nucleic acid sequences from other strong core promoters and/or may be designed at least in part based on known computer programs or promoter databases. Synergy between the potential core elements is determined by standard transcriptional analysis techniques.

Figure 18A:
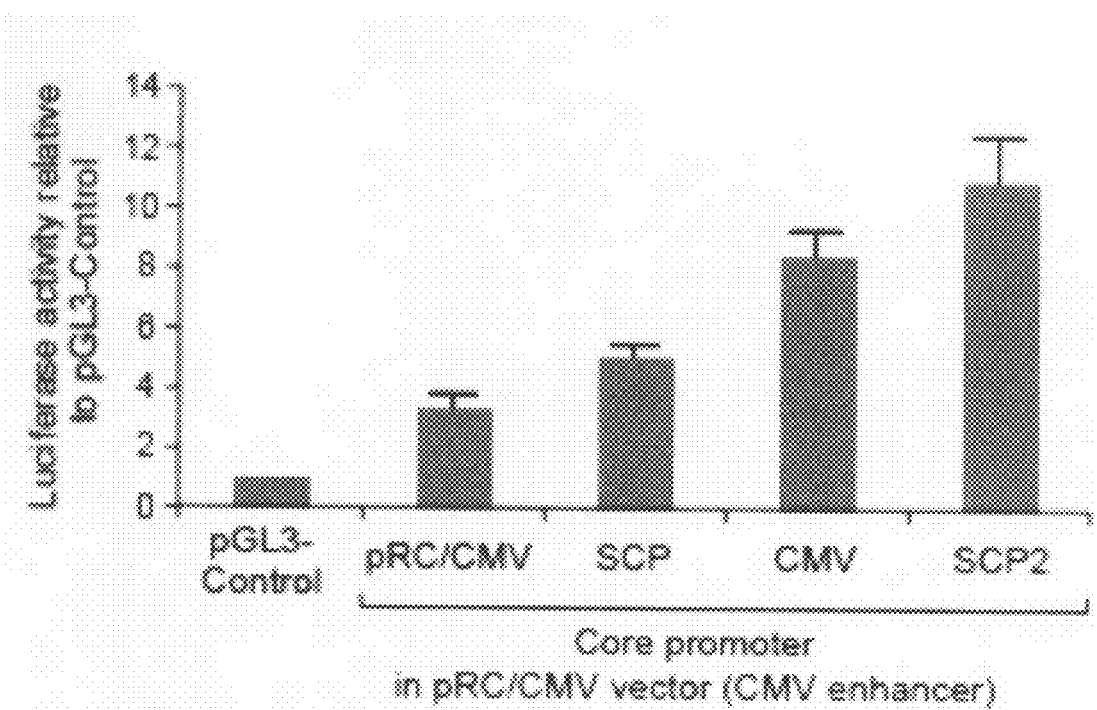
FIGS. 18A-18B show that the SCP strategy can be used to generate new SCPs for different applications. pRC/CMV (Invitrogen) contains the CMV enhancer and TATA box but lacks some CMV sequences, including the Inr, that are downstream of −16 relative to the +1 start site. Three variants of pRC/CMV were constructed in which the core promoter region was replaced with the SCP, the natural CMV core promoter (from −36 to +45), and SCP2, which contains the CMV TATA and Inr, the *Drosophila* Tollo MTE, and a consensus DPE. All pRC/CMV-based constructs contained a luciferase reporter gene.

The nucleic acid sequence comprising a core promoter construct is optimized when the combination and positioning of the core promoter elements within the core promoter construct increases gene expression over that of core promoter constructs with different nucleic acid sequences for the core promoter elements. Additionally, the core promoter function may be optimized by using core promoter elements that are known to act synergistically. An example is the enhanced activity of the natural CMV core promoter in the presence of the CMV enhancer element (FIG. 18A). Thus by combining the CMV TATA and Inr along with an MTE and a DPE sequence an optimized core promoter may be designed. An example of such an optimized core promoter is as shown in SEQ ID NO: 23 and in SEQ ID NO: 61.

Thus, provided herein is an optimized core promoter or super core promoter (SCP) construct comprising optimized core promoter elements Inr, MTE, TATA Box and DPE and other non-negative nucleotides or nucleic acid sequences from other strong core promoters or a consensus of sequences found in the same relative positions to the transcription start site in a metazoan core promoter. Such nucleotides or nucleic acid sequences may be positioned upstream or downstream of the optimized promoter elements to link the optimized elements in operable positions within the super core promoter. Additionally, these non-negative nucleotides or nucleic acid sequences may overlap the Inr or the MTE sequence to form hybrids thereof. Particularly, the non-negative nucleic acid sequences may comprise promoter elements from CMV, AdML and the G element and Krüppel from *Drosophila*.

The SCP may be SCP1 or SCP2 or SCP3 and may have the sequence shown in SEQ ID NO: 8 or 23 or 61, respectively. Alternatively, the SCP may be a variant of SCP1, i.e., SCP-T1 with SEQ ID NO: 59 or variant SCP-T2 with SEQ ID NO: 60. Table 1 shows these sequences. All sequences are from −36 to +45 relative to the +1 transcription start site. Bold depicts the variant nucleotides in SCP-T1 and SCP-T2 com. The underlined nucleotides in SCP3 indicate the differences from SCP2.

TABLE 1

| SEQUENCE DESCRIPTION | SEQUENCE |
|---|---|
| SCP1 (SEQ ID NO: 8) | GTACTTATATAAGGGGTGGGGGCGCG TTCGTCCTCAGTCGCGATCGAACACTC GAGCCGAGCAGACGTGCCTACGGACCG |
| SCP-T1 (SEQ ID NO: 59) | GTACTTATATAAGGGGTGGGGGCGCG TTCGTCTTCAGTTTTTTTTTCAACACTCG AGCCGAGCAGACGTGCCTACGGACCG |
| SCP-T2 (SEQ ID NO: 60) | GTACTTATATAAGGGGTGGGGGCGCG TTCGTCTTCAGTTTCGTTTCAA CACTCG AGCCGAGCAGACGTGCCTACGGACCG |
| SCP2 (SEQ ID NO: 23) | AGGTCTATATAAGCAGAGCTCGTTTAGTG AACCGTCAGATCGCCTGGAGACGTCGAGC CGAGTGGTTGTGCCTCCATAGAA |
| SCP3 (SEQ ID NO: 61) | AGGTCTATATAAGCAGAGCTCGTTTAGTGA ACCGTCAG<u>T</u>CCGCCTGGAGAC<u>C</u>TCGAGCC GAGTGGT<u>C</u>GTGCCTCCATAGAA |

The sequence of nucleic acids or DNA comprising the core promoter or core promoter element may be chemically synthesized de novo or constructed by any suitable technique of vector construction. For example, given the consensus sequences or specific nucleotide sequences for core promoters and/or core promoter elements that may comprise the constructs described herein, one of ordinary skill in the art can easily determine what sequence of nucleic acids should comprise the core promoter. Thus, DNA having this sequence may be synthesized or oligonucleotides comprising the DNA sequence from which to construct the core promoter may be obtained, for example in plasmids, from readily available sources.

The core promoter sequences may comprise expression vectors, as are known and standard in the art. The core promoter sequences may be introduced into a metazoan host cell, such as, but not limited to HeLa, Chinese hamster ovary cells (CHO), baby hamster kidney cells (BHK), human embryonic kidney cells (HEK-293), or *Drosophila* S2 cells. It is well within the purview of one of ordinary skill in the art to construct expression vectors comprising the core promoters, particularly the super core promoter, and to introduce the same into a host cell using standard molecular biological techniques. Alternatively, one of ordinary skill in the art is well suited to genetically alter a metazoan animal to comprise and express, as a transgenic animal, the nucleic acids inserted within these expression vectors. A useful metazoan animal may be *Drosophila*, a leech, a mouse, or a human.

The present invention also provides kits comprising the core promoter constructs described herein. Such kits further may comprise an expression vector comprising the core promoters. Additionally, the kits may comprise a metazoan cell line capable of having the expression vector introduced therein and of expressing the DNA, genes or other nucleic acid contained therein.

It is contemplated that the introduction of the optimized core promoter, particularly, the super core promoter, by expression vectors will result in increased gene expression in metazoan cells and/or metazoan animals. As such, the core promoters may be operably linked to a gene or other expressible DNA or other expressible nucleic acid, as is known in the art. Such a gene may comprise a reporter gene encoding a reporter protein or peptide for use in a diagnostic or other assay or may comprise a gene encoding a therapeutic compound or a combination thereof. For example, a reporter protein may be, but not limited to, β-galactosidase, a luciferase, a green fluorescent protein or other protein or peptide whose expression directly or indirectly elicits a detectable signal. A therapeutic compound may be, and also not limited to, erythropoietin or tissue plasminogen activator or other pharmacologically important molecule, such as an antibody.

Thus it is further contemplated that the core promoters may be used in commercial applications to increase gene expression and/or recombinant protein production in vivo in cultured metazoan host cells and/or transgenic metazoan animals. It is particularly contemplated that increased gene expression in a human would provide a therapeutic benefit. Alternatively, the core promoters may be used for in vitro transcription experiments. Particularly, in any application therefore, the SCP is a multifunctional promoter in that it would function with both DPE- and TATA-specific enhancers.

The following examples are given for the purpose of illustrating various embodiments of the invention and do not limit the present invention in any fashion.

EXAMPLE 1

Core Promoter Sequences and Plasmids

The initial search for MTE-containing promoters was carried out with a sample of potential MTE-containing promoter sequences that were obtained in the course of the computational analysis of *Drosophila* core promoters (20). After initial studies with these promoters, the entire *Drosophila* genome database (Berkeley *Drosophila* Genome Project; http://www.fruitfly.org) by using the JDSA program, available at http://www.biology.ucsd.edu/labs/kadonaga/JD-SA.html, was searched to identify potential MTE-containing core promoters, that had the MTE consensus sequence, CSARCSSAACGS (SEQ ID NO: 1) (20), at precisely +18 to +29 relative to the A+1 position of a canonical Inr consensus sequence.

The plasmids that were used to map the in vitro start sites (FIG. 2B) were constructed by PCR amplification of *Drosophila* genomic DNA with primers that yielded a 300-bp fragment of each promoter from −150 to +150 of the expected RNA start site. These promoter fragments were then cloned into the pGEMT-easy vector (Promega). The minimal core promoter templates, which were used in FIGS. 3-10, were constructed by insertion of double-stranded oligonucleotides into the XbaI and PstI sites in the polylinker of pUC119. Typically, the minimal core promoters include sequences from −36 to +45 relative to the A+1 site. In the mInr mutants, the native Inr sequences were replaced with GTGACA (SEQ ID NO: 13).

The Tollo minimal promoter spacing mutants were generated by insertion of A between T+16 and T+17 (+1), insertion of AAA between T+16 and T+17 (+3), deletion of T+16 (−1), and deletion of A+14 through T+16 (−3). The hybrid hbP2Tollo and hbP2-CG10479 promoters were constructed as follows: First, double-stranded oligonucleotides comprising the −36 to +10 sequences of the hbP2 promoter were inserted into the XbaI and PstI sites of pUC119 to give the pUChbP2 plasmid; then, double-stranded oligonucleotides comprising the +16 to +40 sequences of Tollo or CG10479 were inserted into the PstI site of the pUChbP2 plasmid. The plasmids used in transient transfection assays were constructed by subcloning the Tollo minimal core promoters into the pGL3-Basic expression vector (Promega).

EXAMPLE 2

In Vitro Transcription Analysis

Transcription reactions were carried out as described (21-22) by using supercoiled DNA templates (250 ng or 500 ng) with either *Drosophila* nuclear extracts (23) or HeLa (human) cell nuclear extracts (24). The resulting transcripts were subjected to primer extension analysis with the M13 reverse sequencing primer AGCGGATAACAATTTCACACAGGA (SEQ ID NO: 9) with pUC119 constructs, the CYLuc2 primer AGTACCGGAATGCCAAGCTTAATTAGATCG (SEQ ID NO: 17) with pGL3-Basic constructs, the TGluc3 primer TCTTCCAGCGGATAGAATGGCGCC (SEQ ID NO: 18) with pGL3-Enhancer constructs and the CAT-PE primer ACTTCTGCAGTTAAGCGGCCGCAA (SEQ ID NO: 19) with pCAT3-Enhancer constructs. Quantitation of reverse transcription products was carried out with a PhosphorImager (Molecular Dynamics). All experiments were performed a minimum of three times to ensure reproducibility of the data.

Figure 12A:
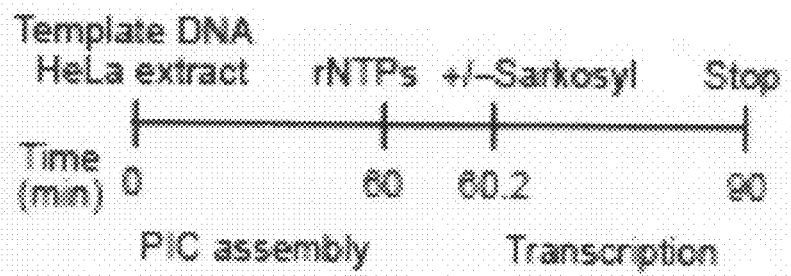
FIGS. 12A-12C show that the SCP is transcribed more efficiently than the CMV or AdML core promoters. Single round transcription reactions were performed as indicated in the diagram in FIG. 12A by using the detergent Sarkosyl. The template usage was determined by quantitation of the primer extension products of the transcripts generated in each single round transcription reaction (FIG. 12B).
Figure 12B:
Figure 12C:
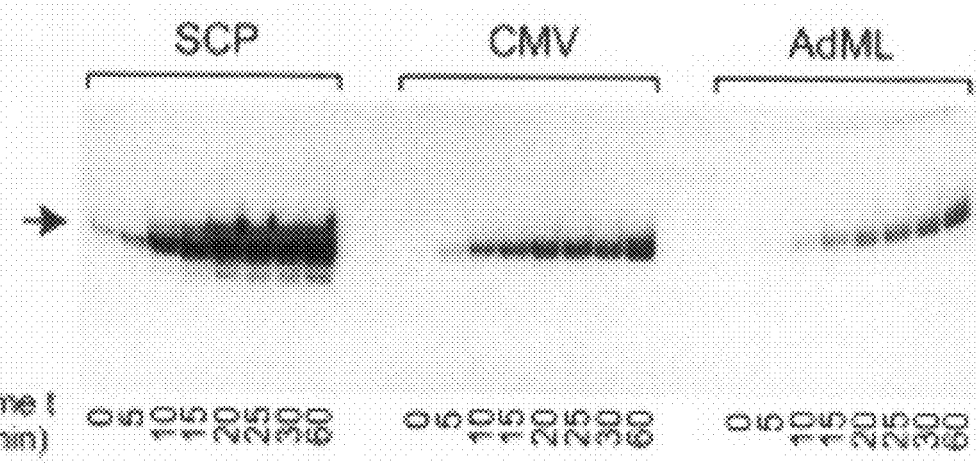

To measure the usage of template DNA, single round transcription reactions were performed by using the anionic detergent Sarkosyl (25, 26, 27). As outlined in FIG. 12B-12C, preinitiation complex (PIC) assembly was allowed to occur with 500 ng of DNA template (containing core promoters in pGL3-Basic vector) for 60 min in the absence of ribonucleoside 5'-triphosphates (rNTPs). Upon addition of rNTPs, transcription initiation occurs rapidly. After 10 sec, Sarkosyl (0.2%, w/v, final concentration) was then added to inhibit transcription reinitiation but not elongation, and thus limit transcription to a single round. The resulting transcripts were then subjected to primer extension analysis, and the reverse transcription products were quantitated (relative to a known amount of labeled primers) with a phosphorimager.

EXAMPLE 3

DNase Footprinting Analysis

DNase I footprint probes were prepared by PCR amplification of each promoter with unlabeled M13 universal primer (upstream) and 5'-$^{32}$P-labeled M13 reverse sequencing primer (downstream) flanking the promoter region. The PCR amplification products were purified with Microspin S300HR columns (Amersham Pharmacia Biotech). TFIID was purified to ~90% homogeneity from *Drosophila* embryos by using a combination of DNA affinity and immunoaffinity chromatography. Footprinting reactions were carried out as described (13).

EXAMPLE 4

Transient Transfection and Reporter Gene Assays

HeLa-S3 cells were cultured in DMEM supplemented with 10% FBS, and were transfected in 60 mm plates by using the Effectene reagent (Qiagen), as recommended by the manufacturer. For luciferase assays, HeLa-S3 cells were plated at $0.5 \times 10^6$ cells per 60 mm plate one day prior to transfection. Cells were transfected with 0.6 µg of each of the various promoter-luciferase constructs along 0.4 µg of a β-galactosidase expression vector. Transfection complexes were removed 6 to 8 hours after transfection, and fresh growth medium was added. Cells were harvested and assayed for luciferase and β-galactosidase activities at 24 to 28 h posttransfection by using the Luciferase Assay and Beta-Galactosidase Enzyme Assay systems (Promega), as recommended by the manufacturer. To correct for transfection efficiency, the luciferase activity of each sample was normalized to the corresponding β-galactosidase activity. The reported values represent the average of triplicate samples in a single experiment. To ensure reproducibility, each experiment was performed a minimum of three independent times. The transfection experiments were performed under conditions in which the template DNA was the limiting component.

CHO cells were cultured in DMEM/F12 media supplemented with 5% FBS, and were transfected with the indicated enhancer-promoter-luciferase constructs by using the Effectene reagent (Qiagen, Valencia, Calif.), as with HeLa S3 cells, except that $0.36 \times 10^6$ CHO cells were added to each 60 mm plate one day prior to transfection. For CAT assays, HeLa-S3 cells were plated at $0.25 \times 10^6$ cells per 60 mm plate one day prior to transfection. Cells were transfected with 50 ng of each of the various promoter-pGL3EnhancerCAT constructs along with 0.55 µg of pBlueScript plasmid (Stratagene, La Jolla, Calif.) and 0.4 µg of a β-galactosidase expression vector (pOG33-SV40 beta-gal). Transfection complexes were removed 6 to 8 hours after transfection, and fresh growth medium was added. Cells were harvested and assayed for luciferase and β-galactosidase activities at about 28 h post transfection by using the CAT Assay and Beta-Galactosidase Enzyme Assay systems (Promega, Madison, Wis.), as specified by the manufacturer. To correct for transfection efficiency, the CAT activity of each sample was normalized to the corresponding β-galactosidase activity. The reported values represent the average of triplicate samples in a single experiment. To ensure reproducibility, each experiment was performed a minimum of three independent times.

EXAMPLE 5

Mapping of Transcription Start Sites in HeLa-S3 Cells

HeLa-S3 cells were transfected in 60 mm plates by using the Effectene reagent (Qiagen), as described above. Cells were transfected with plasmids containing the SCP, CMV or AdML core promoters in the pGL3-Enhancer vector along with 0.4 µg of a β-galactosidase expression vector (pOG33-SV40 beta-gal). At 24 to 27 h posttransfection, cells were harvested, and total RNA was isolated by using the RNeasy kit (Qiagen). Total RNA (30 µg) derived from each sample was subjected to primer extension analysis with TGLuc3 (specific to the pGL3-Enhancer) primer alone, or with both TGLuc3 and a LacZ-specific primer TCCCAGTCAC-GACGTTGTAAAACGAC (SEQ ID NO: 20), which was used as a control for potential variations in transfection efficiency. Primer extension products were resolved on an 8% denaturing polyacrylamide gel along with DNA sequencing reactions of the corresponding constructs that were being analyzed.

EXAMPLE 6

The Motif 10 Sequence was Located at Positions +18 to +29 in the Core Promoter A computational analysis of core promoter sequences in *Drosophila* (20) identified four overrepresented sequence motifs that were located at a distinct position relative to the transcription start site. These four motifs were the TATA-box (motif 3), Inr (motif 4), DPE (motif 9), and a new sequence termed motif 10. Motif 10 was found to be located downstream from the transcription start site in the vicinity of +20 to +30. Next, whether motif 10 was involved in transcription by RNA polymerase II was examined. Given the downstream location of motif 10, it also seemed possible that it could be a variant of the DPE. To investigate the function of motif 10, motif 10-containing core promoter sequences that were identified in Ohler et al. (2002) (20) were examined. This analysis suggested that the motif 10 consensus sequence (CSARCS-SAACGS; SEQ ID NO: 1) was located from +18 to +29 relative to the A+1 position in the Inr. By using the JDSA search program, the *Drosophila* genome database was surveyed for sequences (which were upstream of an open reading frame) that contained a motif 10 consensus sequence from +18 to +29 relative to A+1 of a consensus Inr sequence (FIG. 2A). None of these sequences appeared to contain a TATA-box in the −20 to −30 region upstream of A+1.

Figure 2B:
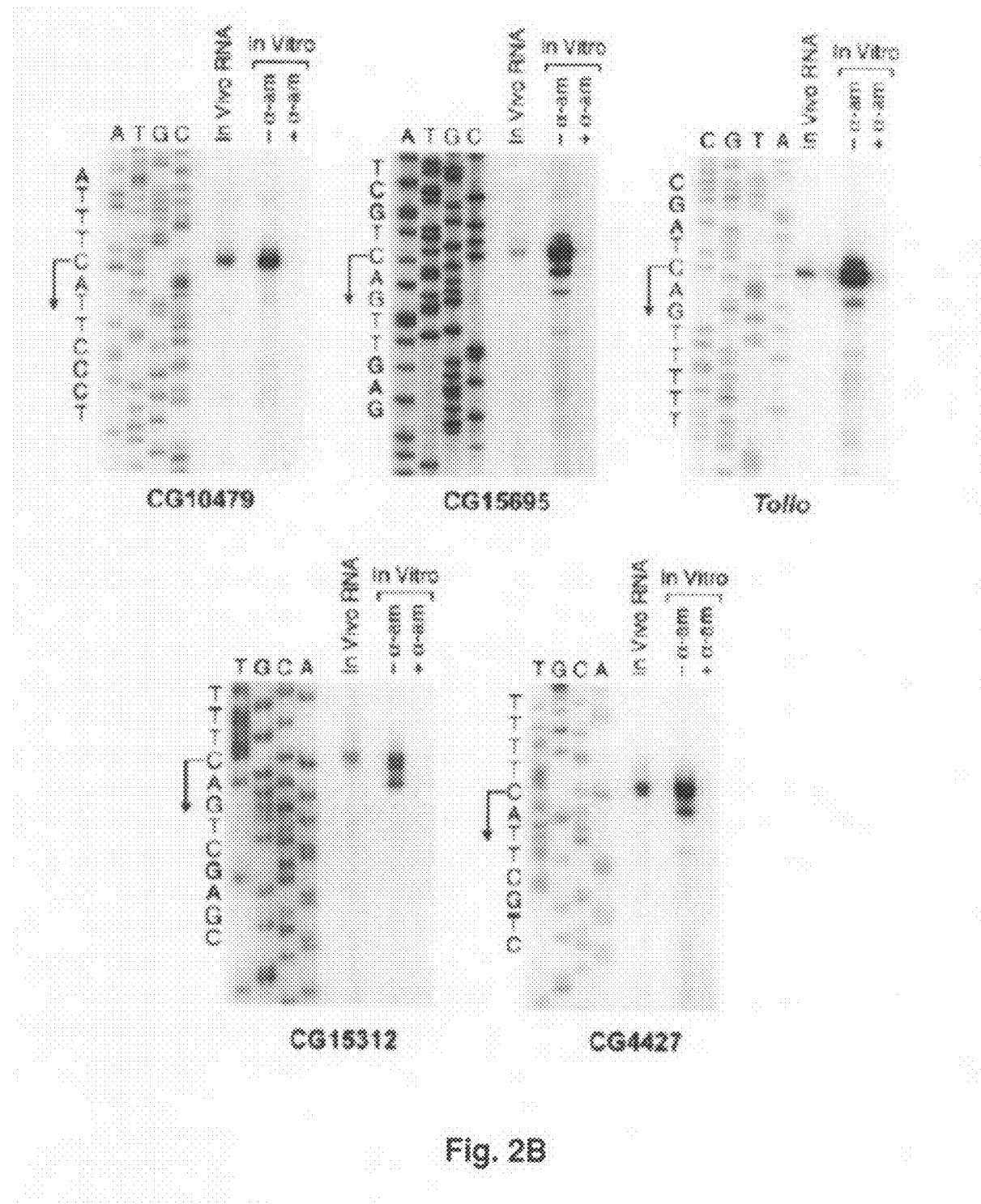

To determine whether these motif 10-containing sequences functioned as core promoters in vivo, primer extension analyses of poly(A)+ RNA that was isolated from *Drosophila* embryos was performed. It was observed that the nine sequences as listed in FIG. 2A were indeed the sites of transcription initiation in vivo (FIG. 2B). In addition, in vitro transcription reactions revealed a correlation between the in vivo and in vitro start sites (FIG. 2B). Transcription from these motif 10-containing promoters appeared to initiate at the "C−1" position of the Inr consensus sequence. For consistency of nomenclature, "A+1" is the "+1" position. Additionally, it was also observed that transcription in vitro was inhibited by 4 μg/mL α-amanitin (α-am; FIG. 2B), which indicated that the transcription was mediated by RNA polymerase II.

EXAMPLE 7

Motif 10 Contained a Promoter Element Termed the MTE

Figure 3:
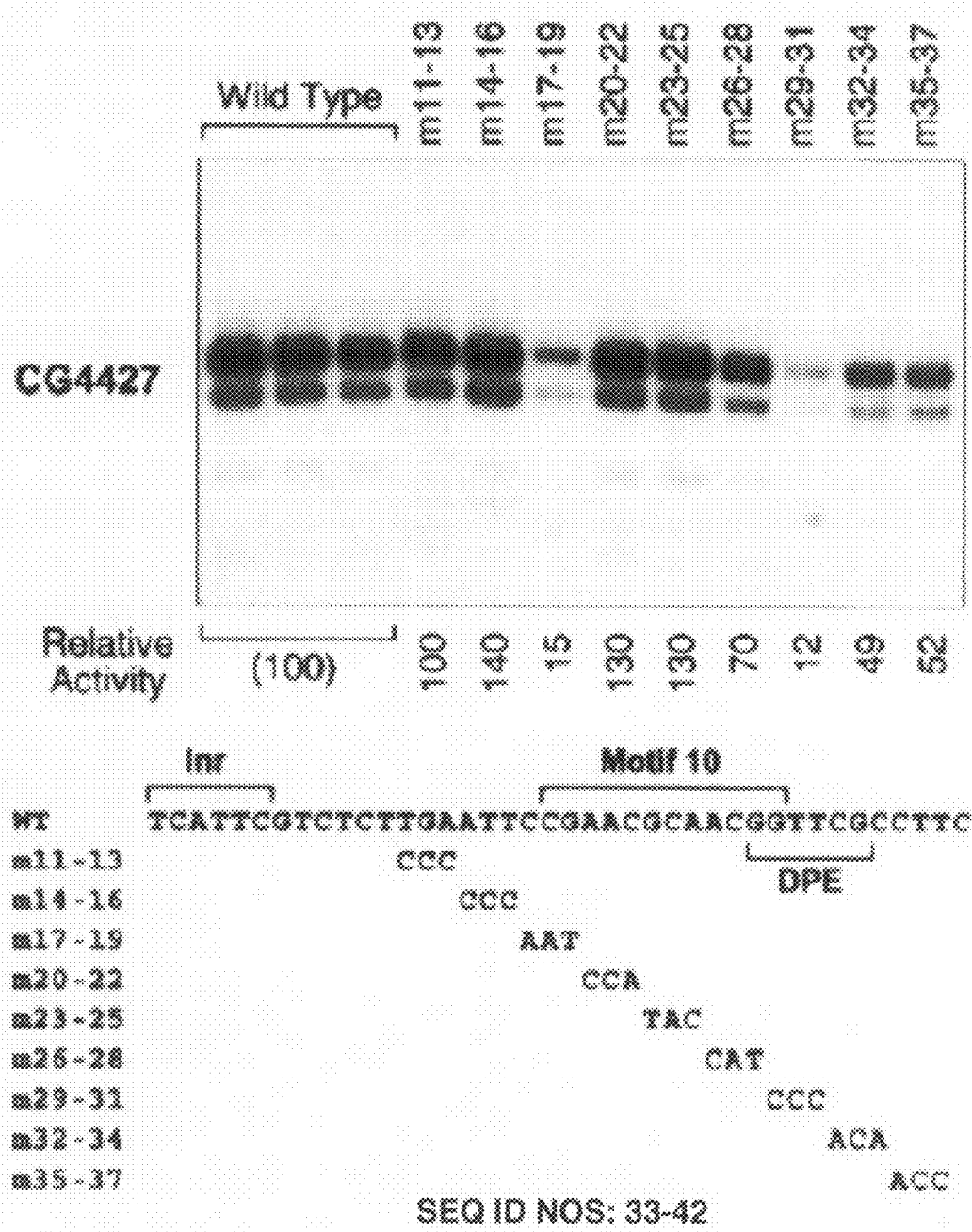
FIG. 3 shows the scanning mutational analysis of the motif 10 sequence. A series of mutant CG4427 core promoters were constructed in which triple nucleotide substitutions were introduced in the downstream promoter region that encompassed the motif 10 sequence and the DPE. Outside the motif 10 sequence, A, T and G nucleotides were mutated to C and C nucleotides were mutated to A. Within the motif 10 sequence the substitution mutations were designed to minimize the similarity of the sequence to the motif 10 consensus. The wild-type and mutant promoters were subjected to in vitro transcription analysis with a *Drosophila* nuclear extract. The transcriptional activity of each mutant promoter was reported relative to that of wild type promoter.

Further, to test whether motif 10 contained a promoter element, a scanning mutational analysis of the downstream region of two motif 10-containing promoters, CG4427 and CG15312 was performed. In these experiments, a series of triple substitution mutations that spanned from positions +11 to +37 was generated, and then the wild-type and mutant promoters were subjected to in vitro transcription analysis. With the CG4427 promoter, mutation of +17-19 as well as +29-31 resulted in a strong decrease in transcription, whereas mutations within the +20-27 region of motif 10 had little or no effect on transcription levels (FIG. 3). Similarly, it was observed that mutations in the +17-19 and +29-31 positions in the CG15312 promoter led to a reduction in transcriptional activity, whereas mutations in the +20-27 region did not result in a significant loss of activity. These results suggested that the +17-19 and +29-31 regions were important for transcription from these two motif 10-containing core promoters.

One feature of motif 10 was the presence of the tandemly repeated AACGGAACGG (SEQ ID NO: 10) motif in the consensus sequence. Mutation of this repetitive sequence had little effect on basal transcriptional activity (FIG. 3). It was possible, for instance, that this motif was a recognition site for a sequence-specific DNA-binding factor that did not participate directly in the basal transcription process. It is contemplated that the motif 10 sequence might comprise two different elements—the MTE and the AACGGAACGG (SEQ ID NO: 10) motif. However, the motif 10 sequence (+18 to +29) overlapped with the DPE consensus (+28 to +33). Hence, the sensitivity of the +29-31 mutants in the CG4427 and CG15312 promoters could be due to the presence of DPE activity in those promoters. Thus, it was important to determine whether the functions of the motif 10 sequence and the DPE were distinct. In order to do so, mutations that specifically inactivated the DPE but not a motif 10-specific promoter activity, and vice versa were created.

Since the DPE consensus (15) was already known, a mutation that inactivated the DPE but did not alter the region of the motif 10 consensus sequence (+18 through +29) was designed. Since this analysis indicated that the CATA nucleotides (SEQ ID NO: 12) were disfavored and/or underrepresented at positions +30 to +33 of DPE-dependent core promoters, the CATA mutation was introduced at +30-33 (m30-33) in the DPE-containing core promoters of the E74B gene and Doc retrotransposon. In vitro transcription analysis revealed that the m30-33 mutation essentially abolished transcription from these DPE-containing core promoters (FIG. 4A). Next, a mutation that disrupted a motif 10-specific promoter activity but did not overlap with the DPE consensus was created. Based on the results of the scanning mutational analysis (FIG. 3), it was known that the +17 to +19 region was important for basal transcription from two different motif 10-containing promoters. Hence, a series of nested substitution mutations in the 5'-region of the motif 10 sequence in the Tollo core promoter was generated and analyzed. These experiments indicated that mutation of the 5'-region of the Tollo motif 10 sequence resulted in a substantial reduction in transcription (FIG. 4B). These findings, combined with those described below, revealed that the 5'-region of the motif 10 sequence contained a promoter activity that did not overlap with the DPE consensus. This core promoter element in the motif 10 sequence was referred to as the MTE, for motif ten element. For the analysis of the contribution of the MTE to promoter activity, the +18 to +22 substitution mutation (m18-22) was used, because it caused about a sevenfold reduction in transcription and is several nucleotides upstream of the DPE consensus sequence.

Figure 5A:
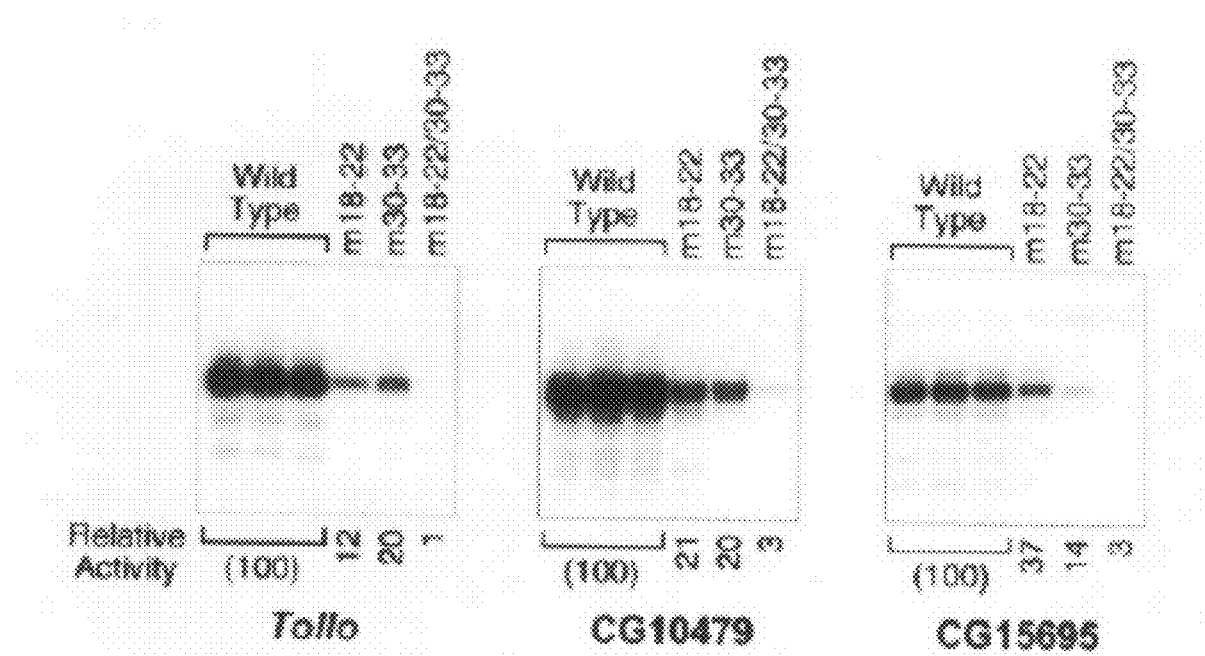
FIGS. 5A-5B show that the motif 10 element (MTE) supported transcription in the absence of the DPE.

To test the contributions of the MTE and the DPE to transcription from MTE-containing promoters, promoters that contained m18-22 (mutant MTE) only, m30-33 (mutant DPE) only, or both m18-22 and m30-33 mutations were constructed and analyzed (SEQ ID NOS: 50-53). The MTE was depicted from +18 to +27 because this segment of the motif 10 consensus was sufficient to confer MTE activity. These analyses were performed with all nine of the MTE-containing promoters shown in FIG. 2A, and the results from three representative promoters are shown in FIG. 5A. These studies revealed that both the MTE and the DPE contributed to transcription from the MTE-containing promoters that were tested. In some promoters, such as Tollo, the MTE appeared to be stronger than the DPE, whereas in other promoters, such as CG15695, the DPE appeared to be stronger than the MTE. These results suggested that the MTE-containing promoters shown in FIG. 5A contained both MTE and DPE elements. In the absence of the DPE, transcription is partially supported by the MTE, and vice versa. Then, in the absence of both the MTE and DPE, transcription is essentially lost.

Figure 5B:
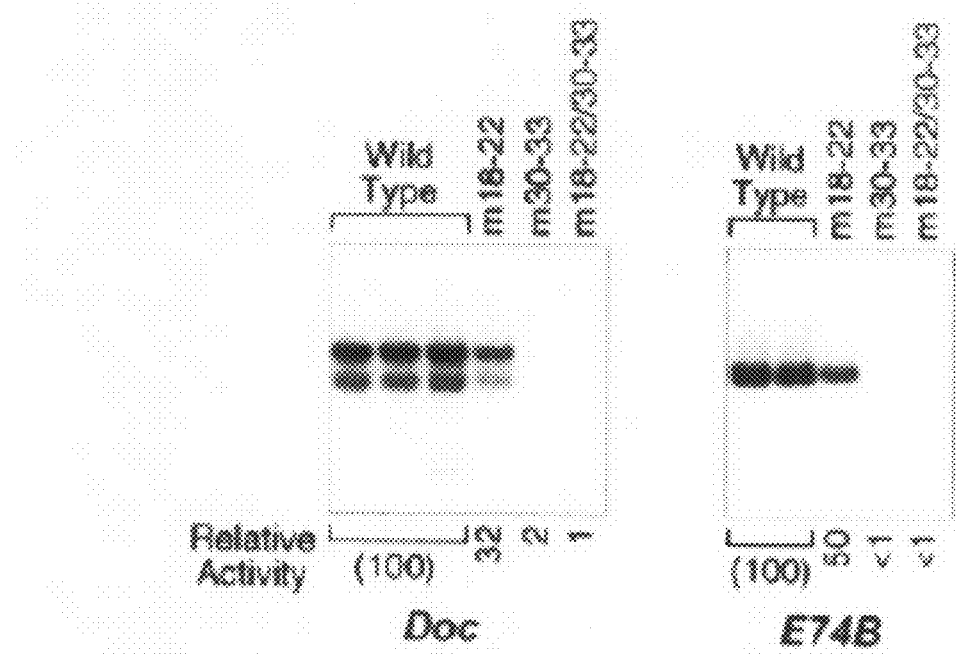

For comparison, the same mutational analysis was performed with two DPE-dependent core promoters (FIG. 5B). Consistent with the results shown in FIG. 4A, the m30-33 DPE mutation caused nearly complete loss of transcription from the E74B and Doc promoters. In contrast, the introduction of the m18-22 MTE mutation resulted in a modest two- to threefold reduction in transcription with these promoters. The strong transcription with the mutant MTE (m18-22) promoters revealed that the E74B and Doc promoters possessed strong DPE activity that could function in the absence of an MTE. In contrast, the nearly complete loss of transcription in the mutant DPE (m30-33) promoters indicated that the E74B and Doc promoters lacked MTE activity that could support transcription in the absence of a DPE. Thus, the E74B and Doc promoters appeared to contain a DPE but not a functionally independent MTE. Thus, several promoters were identified in which both the MTE and DPE were important for transcription as well as two promoters, E74B and Doc, in which the DPE was the predominant downstream promoter element. Promoters that appear to be completely dependent on the MTE have not yet been identified, although the activity of the m30-33 mutant DPE promoters in FIG. 5A suggested that such promoters could theoretically exist. In summary, it was observed that the m30-33 mutation inactivated the DPE (FIGS. 4A, 5B). Then, in the absence of the DPE, transcription from MTE-containing promoters was nearly completely lost upon introduction of the m18-22 mutation (FIG. 5A). Thus, it was concluded that MTE sequences from +18 to +22 were required for MTE-dependent transcription.

EXAMPLE 8

Transcription from MTE-Containing Promoters Requires Precise Inr-MTE Spacing Since the DPE functions with the Inr, whether the MTE had related properties was examined. With the CG15312, CG10479, and Tollo core promoters, mutation of the Inr resulted in an essentially complete loss of transcription (FIG.

Figure 6A:
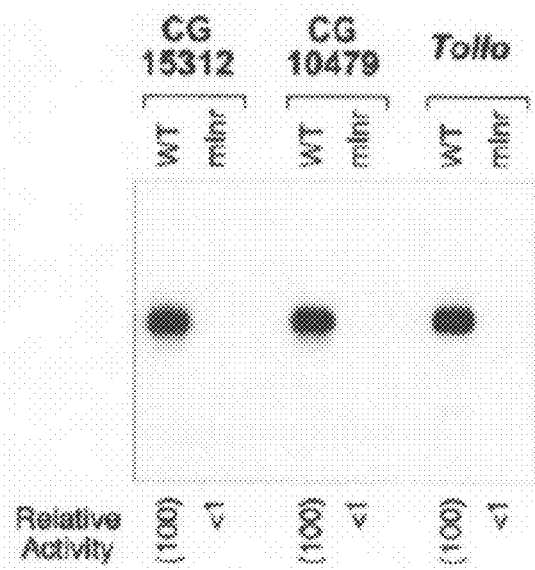
FIGS. 6A-6B show that the MTE functions with the Inr in a spacing-dependent manner.
Figure 6B:
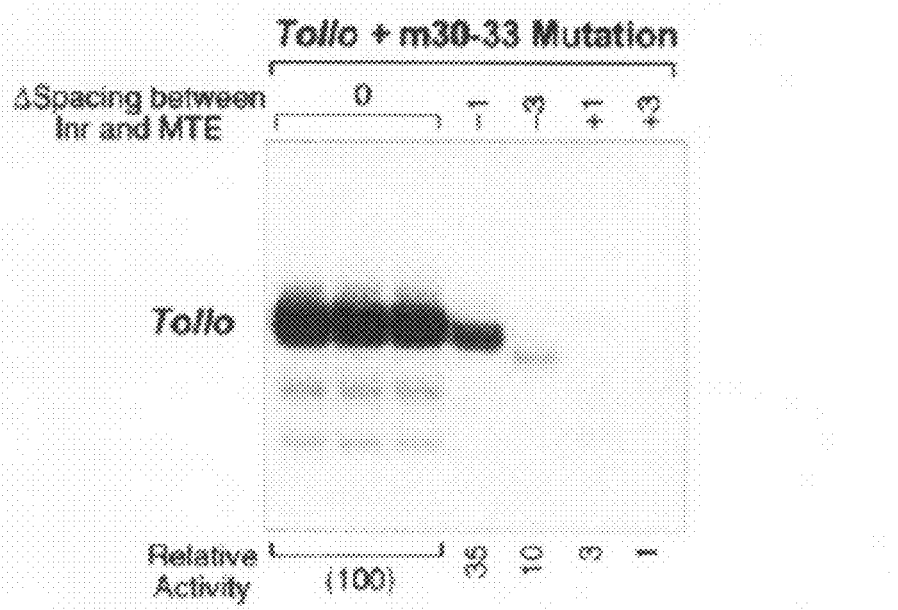

6A). Thus, the Inr was required for transcription from MTE-containing promoters. Whether the spacing between the Inr and MTE was important for transcriptional activity was examined. A series of mutant promoters in which the spacing between the Inr and MTE was increased or decreased by 1 or 3 nt were created (FIG. 6B). To eliminate the contribution of the DPE to transcriptional activity in these promoters, all of the constructions contained the m30-33 DPE mutation. Transcription of the spacing mutant promoters revealed a strong reduction in transcription upon insertion of one or three nucleotides or deletion of three nucleotides between the Inr and MTE sequences. A three-fold reduction in transcription was observed upon deletion of one nucleotide between the Inr and MTE. These results indicated that a strict spacing requirement between the Inr and MTE is important for transcriptional activity.

EXAMPLE 9

MTE:A Distinct Core Promoter Element that Compensates for the Loss of a DPE as Well as Acts Synergistically with the DPE Further, the ability of the MTE to act as a distinct core promoter element was investigated. Since mutation of the MTE resulted in a decrease in transcription, whether the addition of an MTE increased transcription was examined. In this regard, the ability of the MTE to substitute for the loss of the DPE was tested. If the functions of the MTE and DPE were interdependent, then the mutation of DPE could not be restored by the addition of an MTE. On the other hand, if the MTE were independent of the DPE, then the addition of an MTE could potentially restore activity that is lost upon mutation of the DPE. The results from the mutational analysis of MTE-containing promoters (FIG. 5A) suggested that the MTE acted independently of the DPE.

Figure 7:
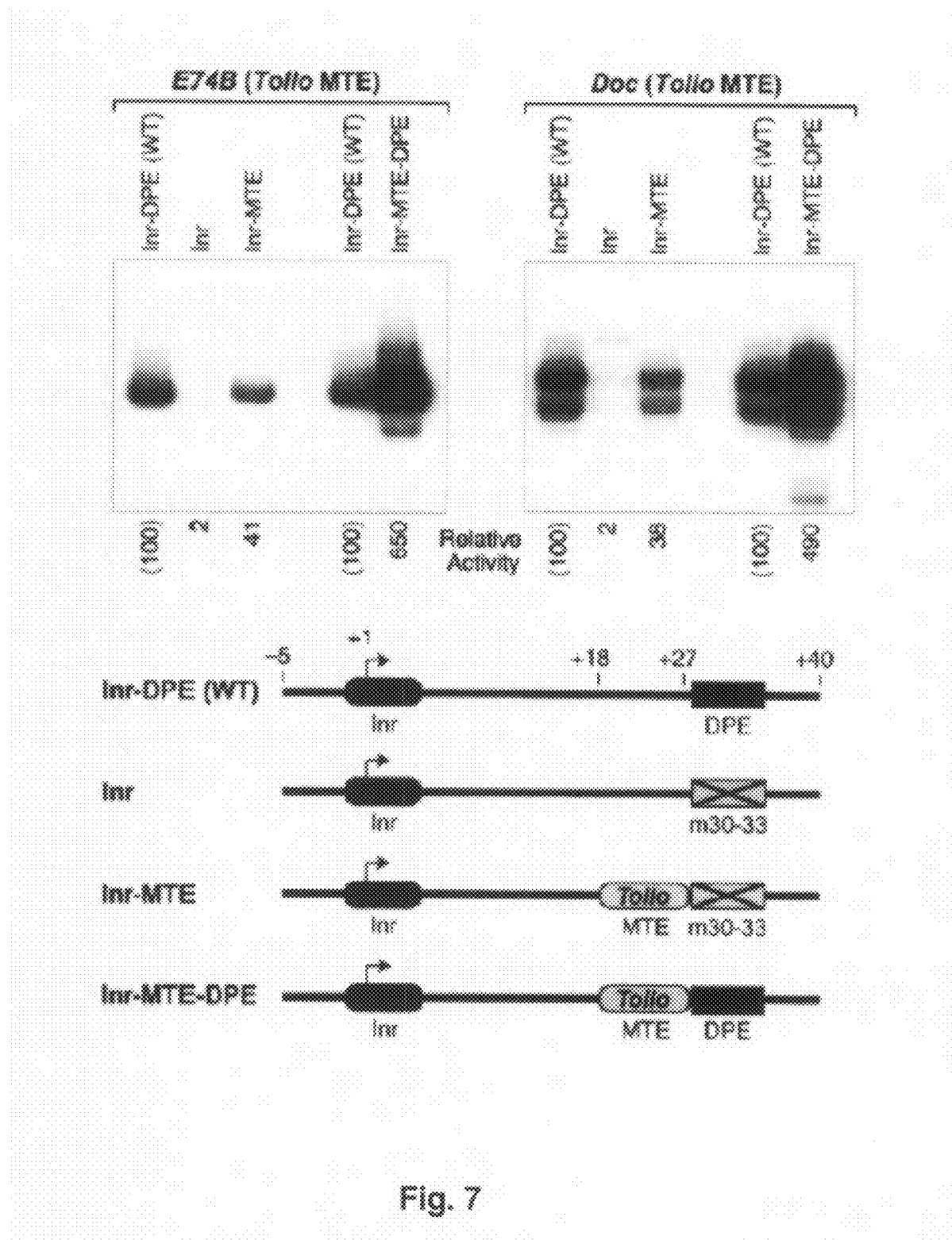
FIG. 7 shows that MTE compensated for the loss of a DPE. The diagram depicts the four variants of the E74B and Doc core promoters that were tested. In the constructs that contained an MTE (Inr-MTE and Inr-MTE-DPE), the +18 to +27 segment of each wild type promoter was replaced by the MTE sequence (from +18 to +27) of the Tollo core promoter. In the Inr and Inr-MTE constructs, the DPE sequence was mutated to CATA (SEQ ID NO: 12) at positions +30 to +33. These E74B and Doc promoter sets were subjected to in vitro transcription analysis with a *Drosophila* nuclear extract. Also, synergy between the DPE and MTE is demonstrated which is important for the design of optimized core promoters and the high activity of the Super Core Promoter. In the left panel, lane 1 is DPE only (relative transcription activity=100); lane 3 is MTE only (activity=41); lane 5 (rightmost lane) is DPE+MTE (relative activity=650, which is much greater than the sum of lanes 1 and 3=100+41=141). In the right panel, lane 1 is DPE only (activity=100); lane 3 is MTE only (activity=38); lane 5 (rightmost lane) is DPE+MTE (activity=490, which is greater than the sum of lanes 1 and 3=100+38=138).

In these experiments, a series of E74B and Doc core promoters, were constructed (FIG. 7). As seen earlier, the introduction of the m30-33 DPE mutation to the E74B promoter or to the Doc promoter resulted in a near complete loss of transcriptional activity (FIG. 7, cf. Inr-DPE and Inr). If, however, the downstream sequences (+18 to +27) from E74B or Doc were substituted with the analogous sequences (+18 to +27) from the Tollo MTE, then core promoter activity was restored to ~40% of wild-type activity (FIG. 7, cf. Inr and Inr-MTE). Thus, the +18 to +27 region of the MTE appeared to be sufficient to compensate for the loss of a DPE in the E74B and Doc core promoters. The +28 and +29 sequences of E74B and Doc, TG and AG, respectively, were not identical to those of Tollo (GG) or to the motif 10 consensus (GS). A strict spacing requirement between Inr and DPE must be present.

Whether there was a synergy between the MTE and DPE motifs was also examined. To this end, variants of the E74B and Doc promoters were constructed in which the wild-type sequences (from +18 to +27) were replaced with the analogous sequences from the Tollo MTE. These experiments revealed potent synergy between the DPE and MTE motifs (FIG. 7, cf. Inr-DPE and Inr-MTE with Inr-MTE-DPE). For example, with the E74B promoter, the activity of the MTE- and DPE-containing promoter (Inr-MTE-DPE) was greater than four times the sum of the activities of the Inr-DPE (WT) and the Inr-MTE promoters. Thus, when combined in a single promoter, the MTE and DPE motifs could function synergistically to facilitate transcription. It might also be noted that the synergism seen in the artificial constructs shown in FIG. 7 resembled the effects seen in the mutational analysis of natural MTE-containing promoters (FIG. 5A). In those experiments, the transcriptional activity of each wild-type promoter was found to be greater than the sum of the activities of the Inr-DPE (m18-22) and the Inr-MTE (m30-33) versions of the promoter. Hence, the MTE could substantially restore the transcriptional activity that was lost upon mutation of the DPE. The results suggested that the +18 to +27 sequences of the motif 10 consensus could confer MTE activity to heterologous core promoters. In addition, the MTE could function synergistically with the DPE. Thus, the MTE was a distinct core promoter element that could function either independently or in collaboration with the DPE.

These findings, together with those in Example 6 demonstrating that the motif 10 sequences from +17 to +22 were most important for MTE transcriptional activity suggest that the 3'-end of the motif 10 sequence is not essential for the basal transcription function of the MTE. In fact, the overlap of the 3'-end of the motif 10 consensus sequence with the 5'-end of the DPE consensus, i.e., positions +28 and +29, might be an artifact of the motif identification algorithm in the computational analysis (20). For instance, an unintended bias at the 3'-end of motif 10 could have arisen from the close and constant spacing between the MTE and DPE and the frequent occurrence of both motifs in the same core promoters.

EXAMPLE 10

Figure 8:
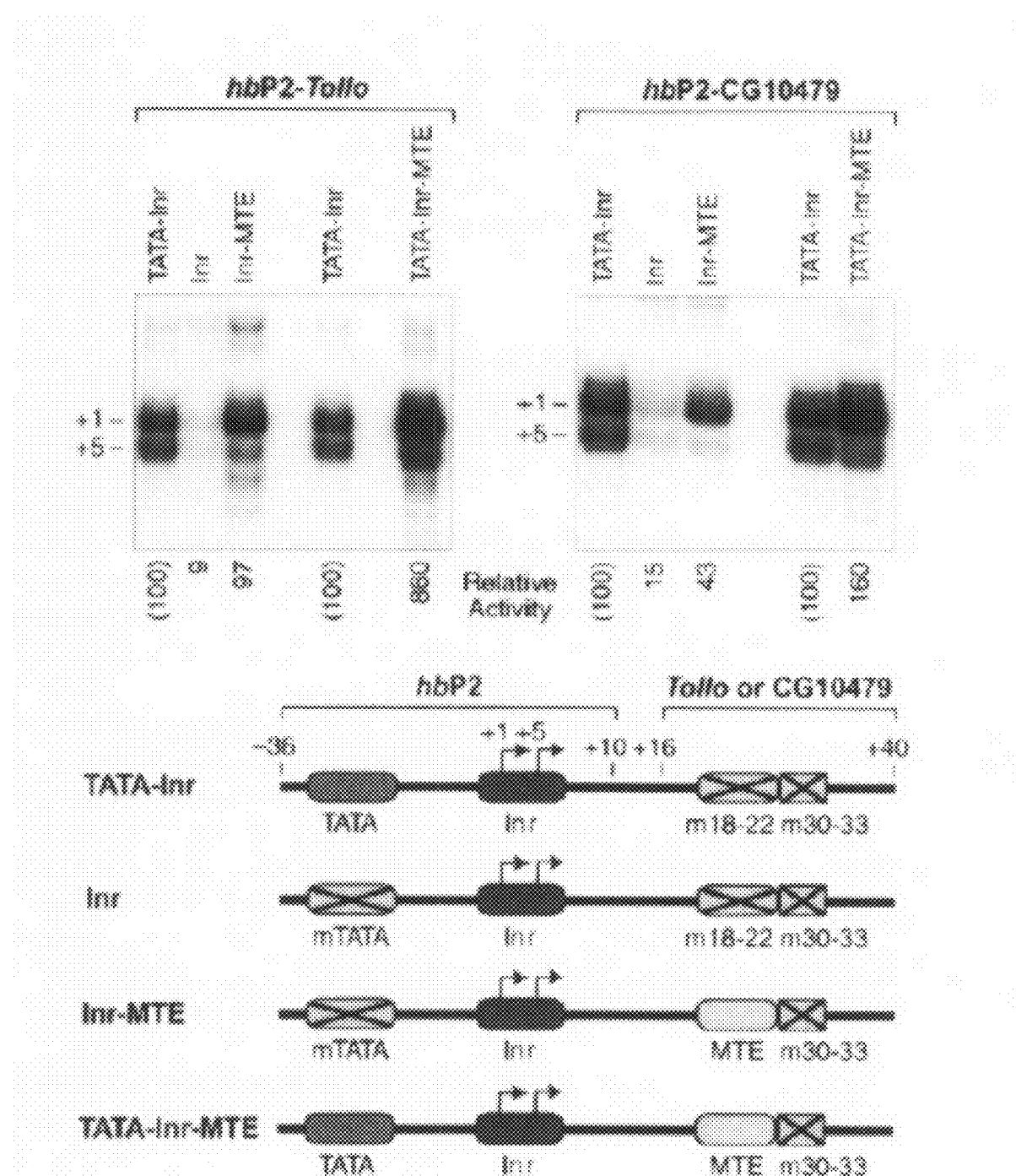
FIG. 8 shows that MTE compensated for the loss of a TATA box. Two sets of hybrid promoters were constructed by fusing the −36 to +10 region of the hbP2 promoter to the +16 to +40 region of either the Tollo or the CG10479 promoter. The hbP2 core promoter contained repeated Inr motifs that directed initiation at +1 and +5. In the hybrid promoters, the spacing of the MTE motifs was aligned with the Inr at +1. To eliminate the contribution of the DPE, all of the promoters contained the m30-33 mutation (CATA at +30 to +33; SEQ ID NO: 12) that inactivated the DPE. The Inr and Inr-MTE constructs contained the mTATA mutation, in which the hbP2 TATA-box, TATATAAA (SEQ ID NO: 14), was replaced by ACGTCGT (SEQ ID NO: 15). The TATA-Inr and Inr constructs contained the m18-22 mutation (ATCCA from +18 to +22; SEQ ID NO: 16), which inactivated the MTE. The hybrid promoter sets were subjected to in vitro transcription analysis with a *Drosophila* nuclear extract, and the transcriptional activity of each hybrid promoter was reported relative to that of the TATA-Inr ("wild type" hbP2) promoter. Also, synergy between the TATA and MTE is demonstrated which is important for the design of optimized core promoters and the high activity of the Super Core Promoter. In the left panel, lane 1 is TATA only (activity=100); lane 3 is MTE only (activity=97); lane 5 (rightmost lane) is TATA+MTE (activity=860>>197=sum of lane 1 TATA only and lane 3 MTE only). The synergy between the TATA box and the MTE is important for the design of optimized core promoters and the high activity of the Super Core Promoter.

The MTE Compensates for the Loss of a TATA-Box as Well as Acts Synergistically with the TATA Box Whether the MTE possesses core promoter activity that could compensate for the loss of a TATA-box was investigated. A series of hybrid promoters were constructed in which the TATA-box and Inr of the hbP2 core promoter were fused to the MTE-containing downstream promoter region of Tollo or CG10479 (FIG. 8). The hbP2 promoter contained a tandemly repeated Inr that directed transcription initiation at two sites that were designated "+1" and "+5." The downstream regions of Tollo and CG10479 were fused to hbP2 such that the MTE was aligned with the Inr that yielded the +1 start site. In addition, all of the promoter constructions contained the m30-33 mutation to eliminate the contribution of the DPE to transcriptional activity.

The TATA-Inr promoters were essentially equivalent to the wild-type hbP2 promoter, because the TATA-Inr promoters consisted of the hbP2 TATA and Inr fused to downstream sequences of Tollo or CG10479 with mutant versions of the MTE and DPE. The TATA-Inr promoters yielded transcripts that initiated from the +1 and the +5 start sites at approximately equal levels. The Inr promoters were identical to the TATA-Inr promoters except that the TATA-box sequences were mutated. As a consequence, the Inr promoters exhibited significantly less transcriptional activity than the TATA-Inr promoters. This loss of activity due to mutation of the TATA-box could be rescued by the addition of an MTE, as seen with the Inr-MTE promoters.

The Inr-MTE promoters contained either the Tollo MTE or the CG10479 MTE in a downstream position in alignment with the Inr motif that directed the +1 start site of the hbP2 promoter. As seen in FIG. 8, the Tollo MTE could almost completely restore the transcriptional activity that was lost upon mutation of the TATA-box. The CG10479 MTE was able to compensate partially (~43%) for the loss of the TATA-box. In addition, there was a strong preference for transcription from the +1 site relative to the +5 site in the Inr-MTE promoters. This bias for the +1 site was most likely due to the alignment of the MTE sequences, which exhibited a strict Inr-MTE spacing requirement (FIG. 6B), with the +1 Inr in the hbP2 core promoter. Thus, these results indicated that the MTE, in the absence of a DPE, could compensate for the loss of a TATA-box.

Whether there was transcriptional synergism between the TATA and MTE motifs was also investigated. A strong synergism was observed between the hbP2 TATA box and the Tollo MTE, as the hybrid promoter that contained both the TATA and the MTE (TATA-Inr-MTE) possessed greater than four times the sum of the activities of the TATA only ("TATA-Inr") and the MTE only (Inr-MTE) promoters (FIG. 8; cf. TATA-Inr, Inr-MTE, and TATA-Inr-MTE for the hbP2Tollo hybrid promoter). However, no synergism was observed between the hbP2 TATA and the CG10479 MTE, although it is contemplated that there are combinations of TATA and DPE motifs that exhibit strong synergism. Based on its ability to rescue the loss of the TATA-box and to function synergistically with the TATA-box, it seemed likely that the Tollo MTE had stronger activity than the CG10479 MTE. Thus, the MTE could compensate for the loss of the TATA-box as well as function synergistically with the TATA-box.

EXAMPLE 11

The MTE is a Recognition Site for the Binding of TFIID to the Core Promoter

The subregion of the MTE that was most important for basal transcription was the 5'-end of the element in the vicinity of +17 to +22 (FIGS. 3, 4A-4B). Thus, the regions of the MTE and DPE that were most important for basal transcription were separated by ~10 or 11 bp, which was roughly one turn of the DNA helix. This arrangement of the MTE and DPE suggested that there might be key contacts of TFIID with the same face of the DNA helix at the MTE and DPE.

Figure 9:
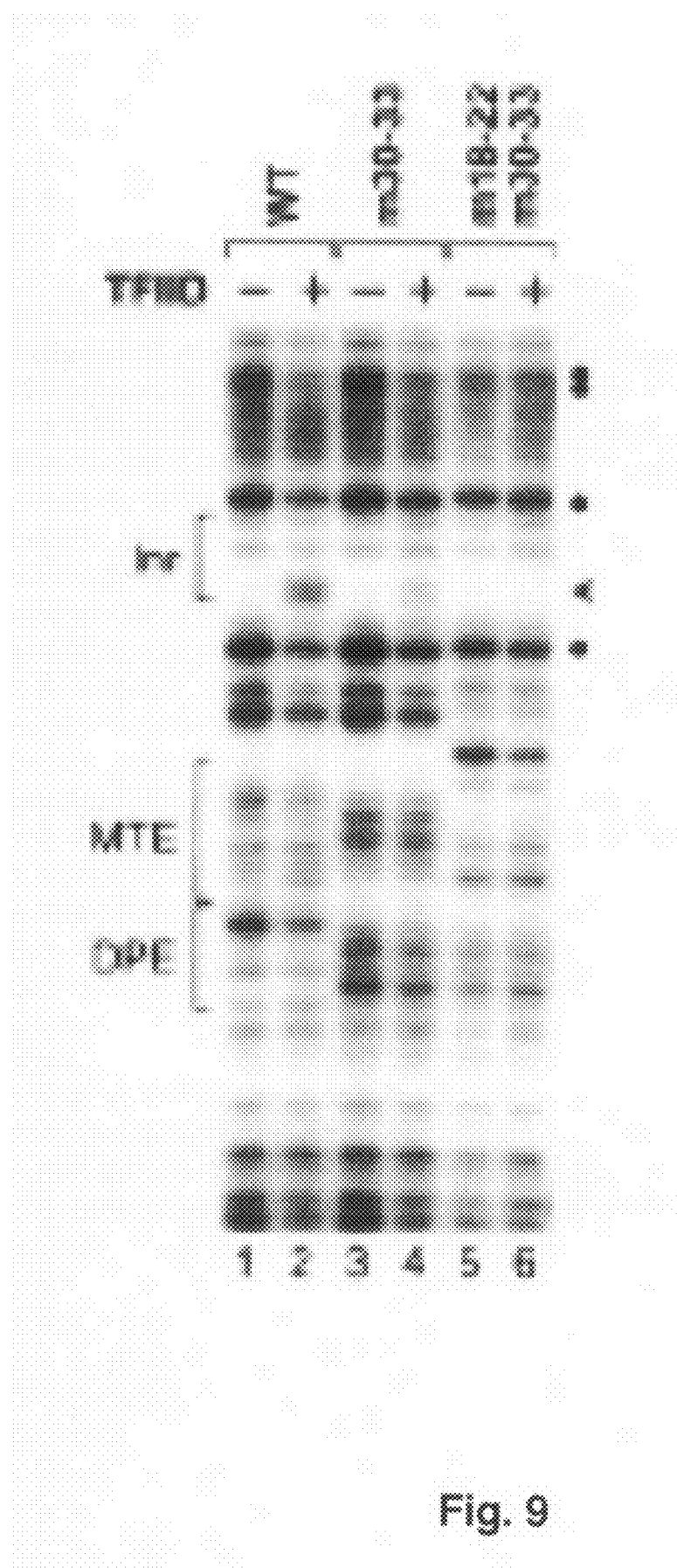
FIG. 9 shows that purified TFIID binds to the MTE. The wild type and m18-22 (mutant MTE) versions of the Tollo core promoter were subjected to DNase I footprinting analysis with purified *Drosophila* TFIID. The binding of TFIID to the wild-type promoter can be seen by the TFIID-induced hypersensitive sites and regions of protection. Upon mutation of the MTE, there is a reduction in the downstream hypersensitive site (between the Inr and MTE) as well as a loss of protection of the region of the promoter that includes the MTE and DPE sequences. These results indicated that the MTE is a recognition site for the binding of the TFIID transcription factor.

TFIID is a key factor in the recognition of the TATA, Inr, and DPE core promoter motifs. Therefore, whether the MTE affected the binding of purified *Drosophila* TFIID to an MTE-containing core promoter was examined. Specifically, it would be interesting to determine the effect of the MTE upon TFIID binding, i.e., comparison of the binding of TFIID to the m18-22 mutant MTE promoter relative to the wild-type promoter. DNase I footprinting experiments were performed with the Tollo core promoter. Two versions of the Tollo promoter were tested, i.e., wild-type and m18-22 (mutant MTE). In these experiments, the binding of *Drosophila* TFIID (of ~90% purity) to the MTE-containing Tollo promoter was observed (FIG. 9, lanes 1-3). Mutation of the MTE resulted in a reduction in a TFIID-induced hypersensitive site between the Inr and MTE, as well as the loss of protection of the downstream region of the promoter that contains the MTE and DPE (FIG. 9, compare lanes 1-3 with lanes 4-6). These results indicated that the MTE is a recognition site for the binding of the TFIID transcription factor.

EXAMPLE 12

The MTE is Recognized by Human Transcription Factors

To investigate whether MTE function is conserved from *Drosophila* to humans, the ability of human transcription factors in HeLa cells to recognize the *Drosophila* Tollo MTE was tested. First, in vitro transcription reactions were performed with wild-type and mutant Tollo core promoters. It was observed that mutation of the MTE resulted in an eight-fold decrease in transcription with a HeLa nuclear extract (FIG. 10A). Additionally, the activity of the Tollo core promoter was tested by transient transfection analysis in HeLa cells (FIG. 10B). In these experiments, the wild-type core promoter exhibited a low level of activity that was only about three- to four-fold higher than that of the promoterless vector. These results reflected the difficulty of studying basal transcription in vivo. Mutation of the core promoter elements resulted in a lower level of activity, but it was not possible to obtain an accurate assessment of the magnitude of the effects.

Next, whether the MTE can compensate for the loss of the TATA-box with human transcription factors was examined. To this end, the hbP2-Tollo hybrid promoter series was used, as in FIG. 7. Transcription of these promoters with human factors revealed that the addition of the Tollo MTE is able to restore partially the loss of transcription upon mutation of the hbP2 TATA box (FIG. 9C; cf. TATA-Inr, Inr, and Inr-MTE). In addition, there was a modest synergism between the TATA and MTE in transcription reactions with human factors (FIG. 9C; cf. TATA-Inr, Inr-MTE, and TATA-Inr-MTE).

Figure 10D:
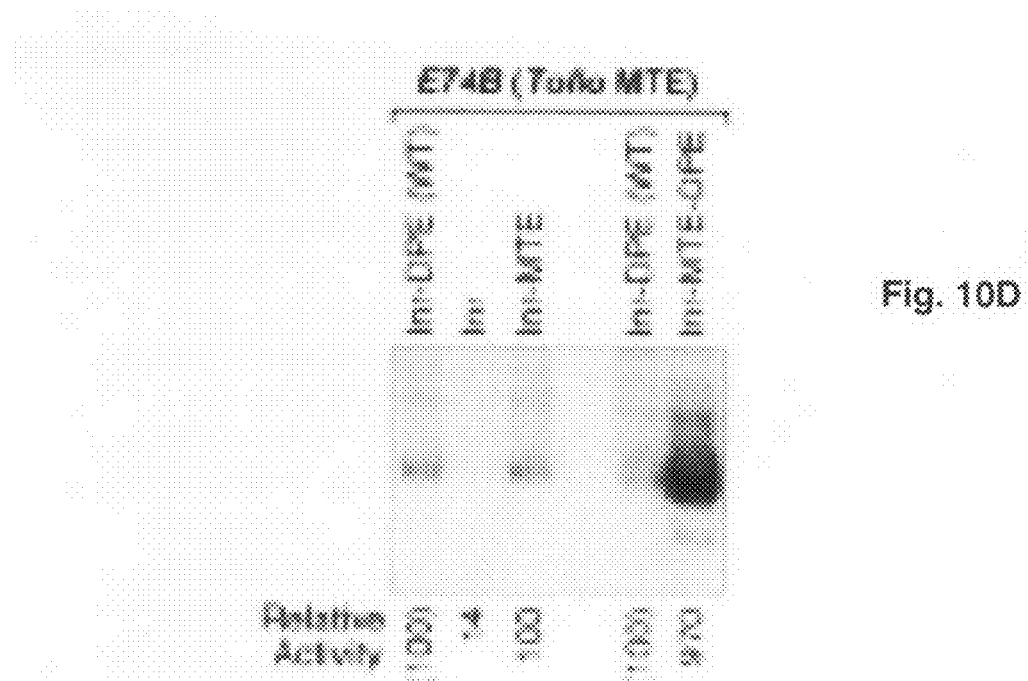

Furthermore, whether the MTE could restore the loss of promoter activity that occurred upon mutation of the DPE in transcription reactions with human factors was also examined. In these experiments, the E74B (Tollo MTE) promoter series that were shown earlier (FIG. 7) were used. With the human factors, the MTE was able to compensate fully for the loss of the DPE (FIG. 10D; cf. Inr-DPE, Inr, and Inr-MTE). Additionally, a potent synergy was observed between the MTE and DPE (FIG. 10D; cf. Inr-DPE, Inr-MTE, and Inr-MTE-DPE), as seen with the *Drosophila* factors (FIG. 7).

Figure 10E:
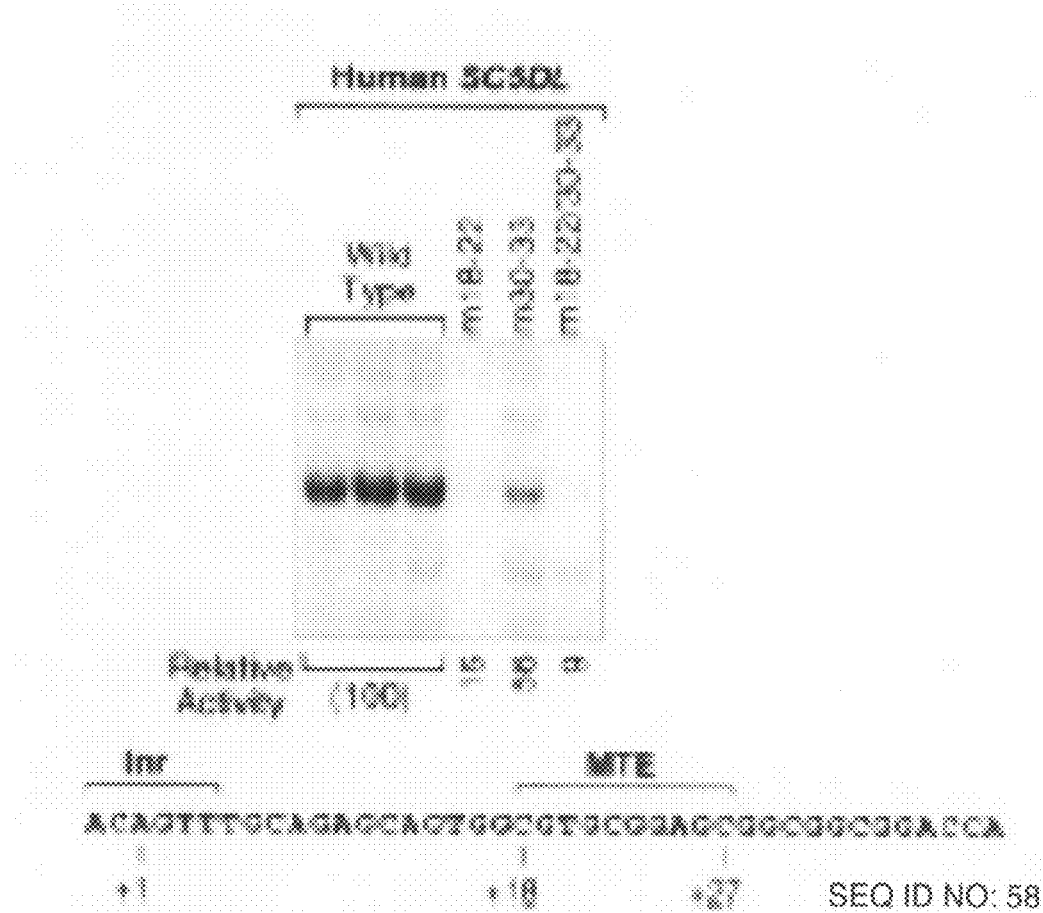

A human core promoter that appeared to contain a functional MTE was identified. As depicted in FIG. 10E, the human sterol C5 desaturase-like (SC5DL; also known as SC5D) promoter (28-29) had sequences that shared similarity with the *Drosophila* Inr and MTE (FIG. 2) but not to the DPE. By primer extension analysis of poly(A)+ RNA from HeLa cells, it was confirmed that the +1 site shown in FIG. 10E was used as a transcription start site in vivo. Additionally, wild-type and mutant versions of the human SC5DL core promoter were constructed and analyzed. These experiments revealed that the m18-22 MTE mutation resulted in about a 6.5-fold decrease in transcription, whereas the m30-33 DPE mutation caused less than a two-fold decrease in transcription (FIG. 10E). These data collectively indicated that the MTE is conserved from *Drosophila* to humans.

EXAMPLE 13

Determine the Functions and Potential Application of Core Promoter Motifs

Since it was observed that the MTE affects the interaction of TFIID with the core promoter, the effects of specific subunits of TFIID upon the ability of TFIID to mediate MTE-dependent transcription is examined by performing cross linking experiments as disclosed (14). Since it was observed that MTE can compensate for loss of TATA box as well as work synergistically with the TATA box, the role of TBP in TATA-less transcription from MTE-dependent core promoters is investigated. Additionally, a similar approach as the one described above is used to investigate whether Motifs 1, 5, 6, 7 and 8 contain core promoter elements.

EXAMPLE 14

Transcription Factors that Mediate Transcription from MTE-Dependent Core Promoters The mechanism of MTE-dependent transcription is related to the mechanisms of DPE- and TATA-dependent transcription is investigated. The MTE functions independently of the TATA box and DPE and hence, MTE-dependent transcription is distinct from TATA- and DPE-dependent transcription. Therefore, the factors involved in MTE-dependent transcription are identified by fractionating and purifying factors from native sources, that is, typically, Drosophila embryos, by using a broad range of assays and approaches.

Furthermore, chromatin immunoprecipitation (ChIP) analysis is used to explore whether there are differences in transcription-related factors at genes containing TATA- vs. DPE- vs. MTE-dependent core promoters. This will identify factors that are present in the upstream, start site, and downstream regions that encompass DPE- vs. MTE- vs. TATA-dependent promoters as well as test factors that are involved in basal transcription and other perhaps less obvious factors that are involved in transcriptional regulation or linked to the transcription process.

EXAMPLE 15

Development of a Super Core Promoter (SCP)

The function of the MTE as a core promoter element was more clearly demonstrated by its ability to increase transcription when added to a heterologous core promoter, i.e., gain-of-function (FIGS. 7-8), than by the loss of transcription upon mutation of the MTE sequences, i.e., loss of function (FIGS. 5A-5B). The mutational analysis of promoter sequences was complicated by the non-existence of transcriptionally neutral nucleotides—hence, there was a good probability that any given nucleotide change would have some effect, which would be most likely negative, if it was in a core promoter region, upon transcriptional activity.

However, the near complete loss of core promoter activity upon mutation of both the MTE and DPE (FIG. 5A) strongly suggests a function of the MTE in the core promoter. It was less likely that an alteration of the core promoter, i.e., the addition of an MTE (FIGS. 7-8) would significantly increase transcription. Also, the strict spacing requirement between the Inr and MTE (FIG. 6B) and the synergy between the MTE and DPE (FIG. 7), as well as between the TATA and MTE (FIG. 8), demonstrated a functional linkage between the TATA, Inr, and DPE core promoter elements and the MTE.

Figure 11A:
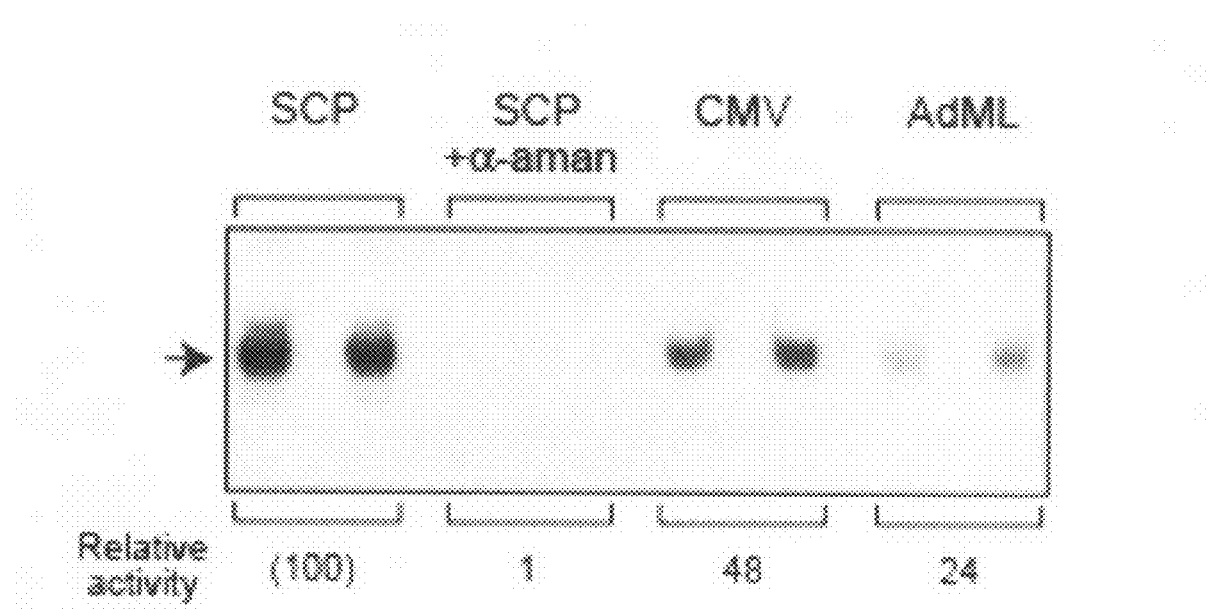
FIGS. 11A-11B show that the super core promoter (SCP) is stronger than the cytomegalovirus (CMV) and adenovirus major late (AdML) core promoters in vitro. Parallel versions of the SCP, CMV, and AdML core promoters (each of which contains their respective sequences from −36 to +45 relative to the +1 start site cloned into pUC119) were subjected to in vitro transcription analysis (in duplicate reactions) with a standard HeLa transcription extract. The resulting transcripts were detected by primer extension. To test whether transcription was catalyzed by RNA polymerase II, a-amanitin (a-aman; 4 µg/mL) was included in the reactions, as indicated (FIG. 11A). The SCP is more active than the CMV or AdML core promoters over a wide range of DNA concentrations as shown in FIG. 11B. Transcription reactions were carried out in a total volume of 50 µL.
Figure 11B:
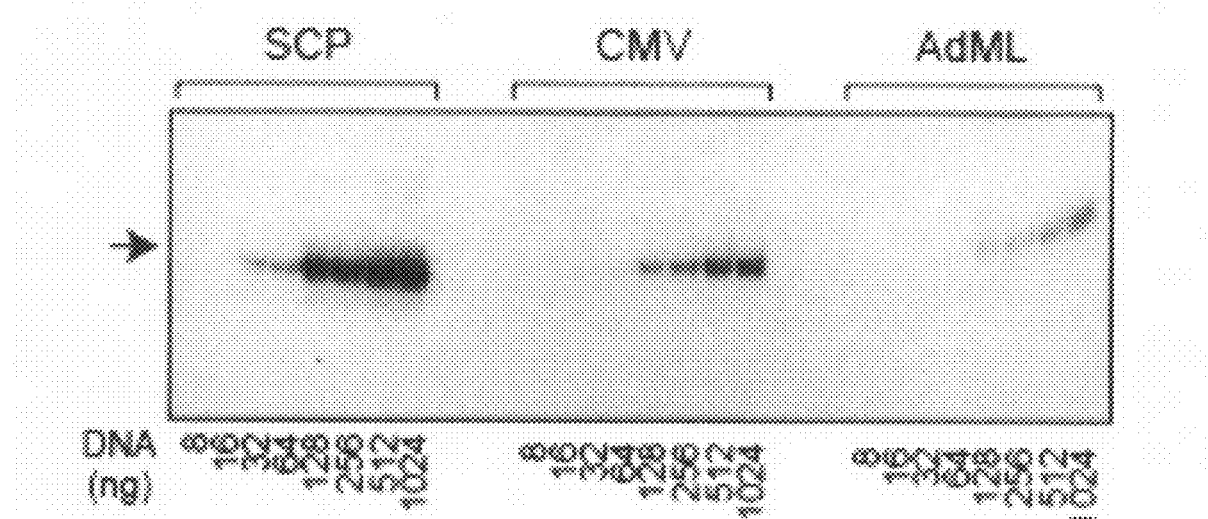

Since a strong synergy was observed between the MTE and TATA box, as well as between the MTE and the DPE, a potent, synthetic core promoter with optimized core promoter elements (TATA, Inr, MTE, DPE) could be designed. Hence, an idealized core promoter, termed the 'super core promoter' (SCP1; SEQ ID NO: 8,) was designed. In in vitro transcription experiments with HeLa nuclear extracts, the super core promoter was several times stronger than either the adenovirus major late core promoter AGGTCTATATAAGCA-GAGCTCGTTTAGTGAACCGTCAGATCGC CTG-GAGACGCCATCCACGCTGTTTTGACCTCCATAGAA (SEQ ID No: 21) or the cytomegalovirus (CMV) immediate early (IE1) core promoter GGGGC-TATAAAAGGGGGTGGGGGCGCGTTCGTC-CTCACTCTCTTCCGCATCGCTG TCTGCGAGGGC-CAGCTGTTGGGGTGA (SEQ ID NO: 22). SCP1 yielded three to ten fold higher amounts of RNA than yielded by the adenovirus major late (AdML) core promoter or the cytomegalovirus (CMV) immediate early core promoter in standard in vitro transcription reactions with HeLa nuclear extracts (FIGS. 11A-11B).

The SCP comprises sequences for Inr, MTE, TATA and DPE, optimized for strong core promoter activity as measured by in vitro transcription. As there is no such thing as "neutral" DNA, sequences upstream, downstream and in between the known core promoter motifs Inr, MTE, TATA Box, and DPE, are identical to known sequences from other known strong core promoters, such as from Drosophila, CMW and AdML, also assessed by in vitro transcription analysis. Thus, the SCP is optimized because these sequences do not inhibit transcription, although they may be non-negative. As the fundamental mechanism of transcription is conserved from Drosophila to humans, Drosophila promoter sequences are functional in humans and vice versa. The SCP comprises the following components. 1) Relative to A+1 in the Inr element in the core promoter, the sequence from −36 to −32 is from the Drosophila Krüppel core promoter selected as being a core promoter sequence that does not contain any positive elements, but rather does not comprise any nucleotides or sequences that would adversely affect transcription. 2) The TATA box sequence from −31 to −24 is identical to the TATA box in the cytomegalovirus immediate early core promoter (CMV), which is a strong TATA-containing core promoter that matches the TATAWAAR consensus sequence (SEQ ID NO: 5). 3) The sequence from −23 to −1 is from the adenovirus 2 major late core promoter (AdML), another strong core promoter. This sequence contains sequences from −23 to −3 which are expected to be non-negative, i.e., contains no negative sequences, as well as TC from −2 to −1 which are the first two nucleotides of the Inr. 4) The sequence from +1 to +16 is from the G element in Drosophila. The core promoter in the G element is the strongest known DPE-dependent core promoter. The G element is a long interspersed nuclear element (LINE), which is a non-long terminal repeat retrotransposon. The sequence from +1 to +4 is a component of the Inr. The sequences from +5 to +16 are non-negative. 5) The Inr of the super core promoter, i.e. from −2 to +4 is a hybrid Inr from the AdML core promoter at −2 and −1 and the G core promoter at +1 to +4. It matches the TACAKY (SEQ ID NO: 4) Inr consensus sequence in the Drosophila and the YYANWYY (SEQ ID NO: 11) in humans except for Y at +5. 6) The sequence from +17 to +27 is from the Drosophila Tollo core promoter. Tollo is the strongest known MTE-containing core promoter. The T at +17 is expected to be non-negative. The sequence from +18 to +27 is the MTE. It is a perfect match with the MTE consensus of CSARCSSAAC (SEQ ID NO: 2) except for position +26 which is G in Tollo and A in the consensus sequence. 7) The sequence from +28 to +45 is from the core promoter of the Drosophila G element, as described supra. The stretch of nucleotides from +28 to +33 is the DPE. It is a perfect match with the DPE consensus sequence RGWYVT (SEQ ID NO: 6). The sequence from +34 to +45 is included as a non-negative sequence.

EXAMPLE 16

Construction of the Super Core Promoter

Oligonucleotides comprising the −36 to +45 of the SCP and flanking nucleotides comprising XbaI (5') and PstI (3') sites were annealed to their complementary oligonucleotides to produce double-stranded DNA. The double-stranded DNA was ligated into XbaI and PstI sites in the polylinker of pUC119 that was previously digested with XbaI and PstI. The ligated DNA was transformed into competent bacteria and colonies were analyzed. Plasmid DNA was prepared from colonies and analyzed. Construction was verified by DNA sequence analysis. The DNA was prepared using the CsCl ultracentrifugation procedure and re-sequenced.

EXAMPLE 17

The SCP is Transcribed More Efficiently than Other Core Promoters

Single round transcription analyses was carried out to determine why the SCP is more active than other core promoters. In a simple model, the RNA polymerase II transcription process can be subdivided into PIC assembly, which occurs in the absence of ribonucleoside 5'-triphosphates (rNTPs) and transcription initiation and elongation, which requires rNTPs. The anionic detergent Sarkosyl inhibits transcription initiation and elongation, which require the rNTPs but not elongation. Thus by addition of Sarkosyl to transcription reactions immediately after the initiation with the rNTPs, it is possible to limit transcription to a single round and to measure the extent of PIC assembly.

A series of single round transcription experiments in which the time of PIC assembly was varied was carried out to monitor the rate of PIC assembly. These experiments revealed that PIC assembly with the SCP is more efficient than that with the CMV or AdML core promoters. However, the rate at which maximal transcription was achieved with the SCP appeared to be similar to that with the CMV or the AdML core promoters. Thus, it appears that transcription from the SCP is more efficient rather than more rapid than transcription from the other core promoters.

The efficiency of transcription with SCP was examined by limiting the transcription to a single round with Sarkosyl (FIGS. 12A-12C) or allowed to proceed for multiple rounds in the absence of Sarkosyl. By comparing the amount of transcription in the absence of sarkosyl relative to the presence of Sarkosyl it was determined that approximately four rounds of transcription occur with the SCP, CMV and AdML core promoters over a 30 min period. These results additionally support the conclusion that the transcription process with the SCP does not occur more rapidly than with the other promoters. In contrast, quantitation of the amount of transcripts synthesized per DNA template in the single round transcription reactions revealed a significantly higher template usage with the SCP (30%) relative to the CMV (11%) or AdML (4%) core promoters. Hence, the strong activity of the SCP appears to be due to a higher level of template usage with the SCP relative to that with the other core promoters.

Figure 13:
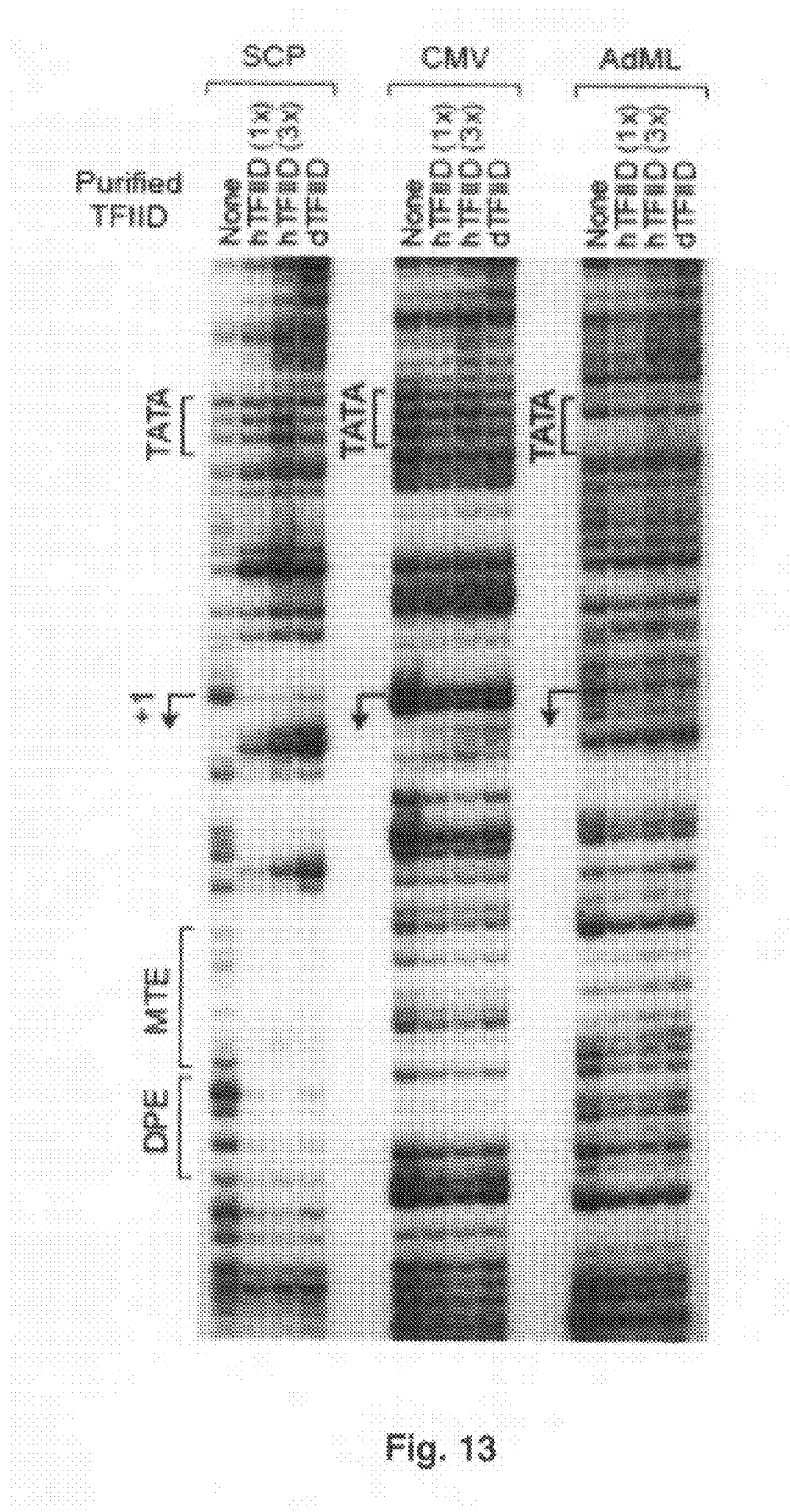
FIG. 13 shows that TFIID binds with higher affinity to the SCP than to the CMV or AdML core promoters. DNase I footprinting reactions were performed with either purified human TFIID (hTFIID; 1× is approximately 30 ng) or purified *Drosophila* TFIID (dTFIID; ~10 ng) in a volume of 50 µL. The locations of the TATA, MTE, and DPE motifs and the transcription start sites are shown.

To investigate the basis for the efficiency of transcription with the SCP, the binding of purified TFIID to the SCP as well as the CMV and AdML core promoter by DNase I footprinting analysis (FIG. 13) was examined. These experiments revealed that purified human TFIID (hTFIID) as well as purified *Drosophila* TFIID (dTFIID) bind to the SCP with higher affinity than to the CMV or AdML core promoters. The binding of TFIID was most evident from the Inr through the MTE and DPE. These results suggest that the high efficiency of transcription from the SCP is due to the higher affinity of TFIID binding to the SCP relative to the other core promoters.

EXAMPLE 18

The SCP is a Strong Core Promoter

Figure 14A:
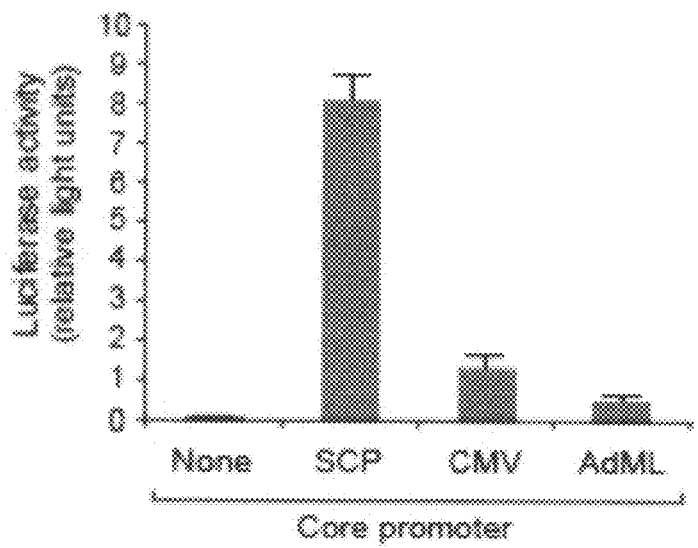
FIGS. 14A-14B show that the SCP is a strong core promoter in HeLa S3 cell line. The SCP is stronger than the CMV and AdML core promoters in vivo. Transient transfection assays were carried out in HeLa S3 cells with constructs containing the SCP, CMV, or AdML core promoters linked to a luciferase reporter gene in the pGL3-Basic vector. A β-galactosidase expression plasmid was also cotransfected as a reference. To correct for variations in transfection efficiency, the luciferase activity of each sample was normalized to its corresponding β-galactosidase activity. Each reported value is the average of triplicate samples (FIG. 14A). To show that each of TATA, Inr, MTE, and DPE motifs contribute to SCP activity, HeLa S3 cells were transfected with constructs containing the SCP or variants of the SCP with mutations in the TATA (mTATA), Inr (mInr), MTE (mMTE), or DPE (mDPE) motifs in the pGL3-Basic vector.

The activity of the SCP was analyzed by transient transfection analysis. These studies address two questions—first, whether the SCP is a strong core promoter in vivo, and second, whether increasing the strength of the core promoter can result in enhanced production of proteins (in this work, luciferase or chloramphenical acetyltransferase) in cells. Initially the core promoter activity of the SCP in the absence of an enhancer was examined. For these experiments, the SCP as well as the CMV and AdML core promoters were subcloned into a promoter-less, enhancer-less vector with a luciferase reporter gene. The constructs were transfected into HeLa S3 cells, and the luciferase activity produced in the cells was measured. As seen in FIG. 14A, the SCP yields several-fold higher levels of luciferase than either the CMV or AdML core promoters.

Figure 14B:
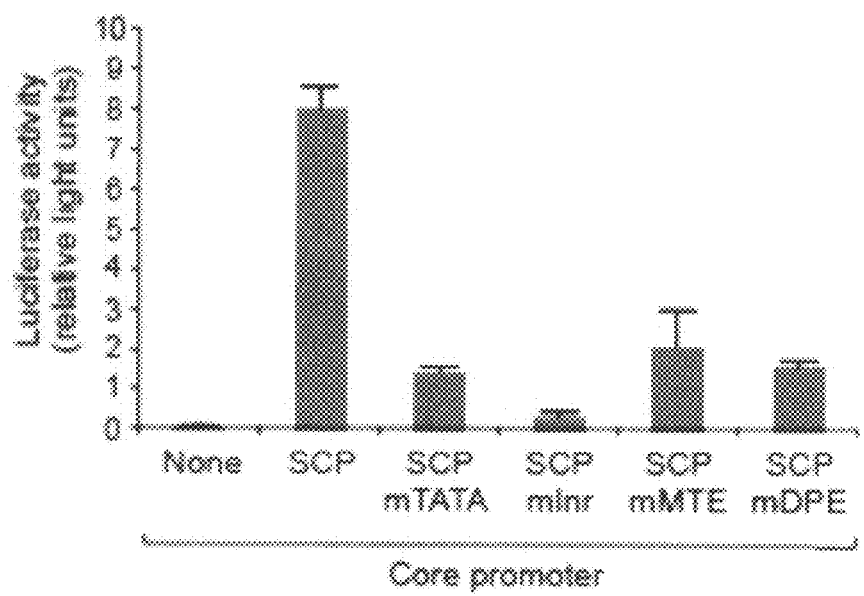

To study the importance of each individual element of the SCP a parallel series of SCP constructs in which the TATA, Inr, MTE, and DPE were each individually mutated were prepared. Transfection of the SCP and mutant versions of the SCP into HeLa S3 cells revealed that each of the core promoter motifs in the SCP contributes about 3-25 fold to core promoter activity in vivo in the absence of an enhancer (FIG. 14B). Thus, the full activity of the SCP requires the presence of each of the core promoter motifs.

EXAMPLE 19

SCP Increases the Level of Enhancer-Driven Transcription

Figure 15:
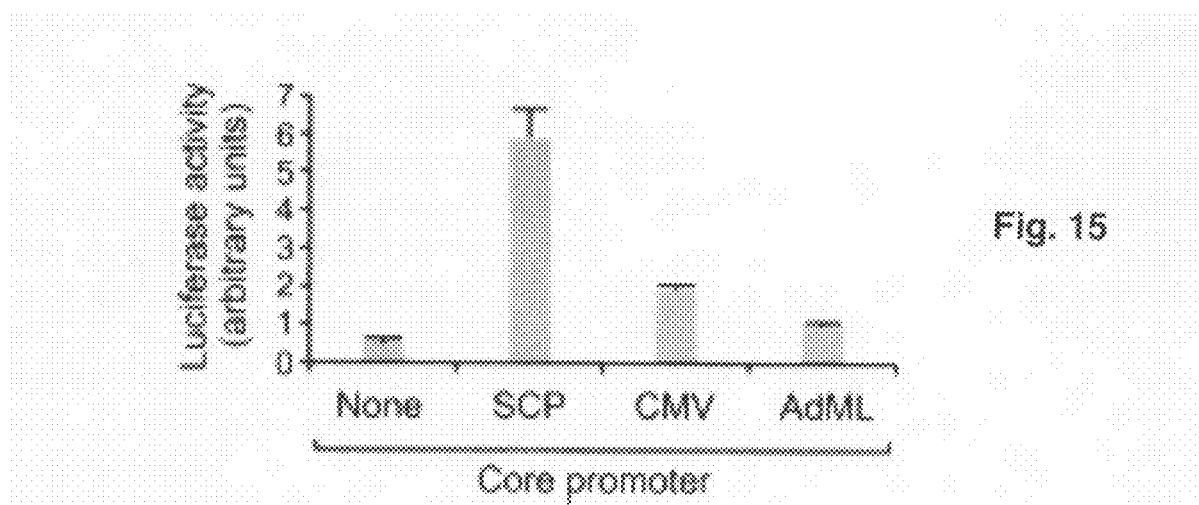
FIG. 15 shows that SCP is more active than the CMV and AdML core promoters in CHO cells.
Figure 16A:
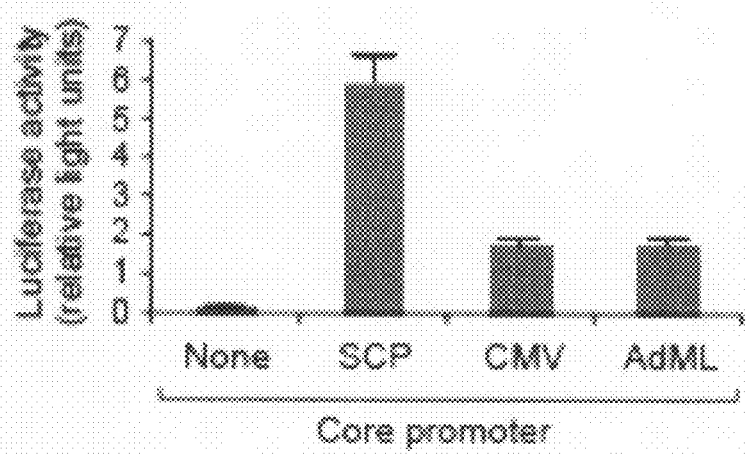
FIGS. 16A-16D show that the SCP yields high levels of activated gene expression in HeLa S3 cells. Transient transfection assays were carried out in HeLa S3 cells with the SV40 enhancer linked to the indicated core promoters with either luciferase (pGL3-Enhancer luciferase vector, FIGS. 16A-16B) or chloramphenicol acetyltransferase (CAT; pCAT3-Enhancer vector, FIGS. 16C-16D) reporter genes. A β-galactosidase expression plasmid was also co-transfected as a reference. To correct for variations in transfection efficiency, the luciferase and CAT activities were normalized to the corresponding β-galactosidase activities. Each reported value is the average of triplicate samples.
Figure 16B:
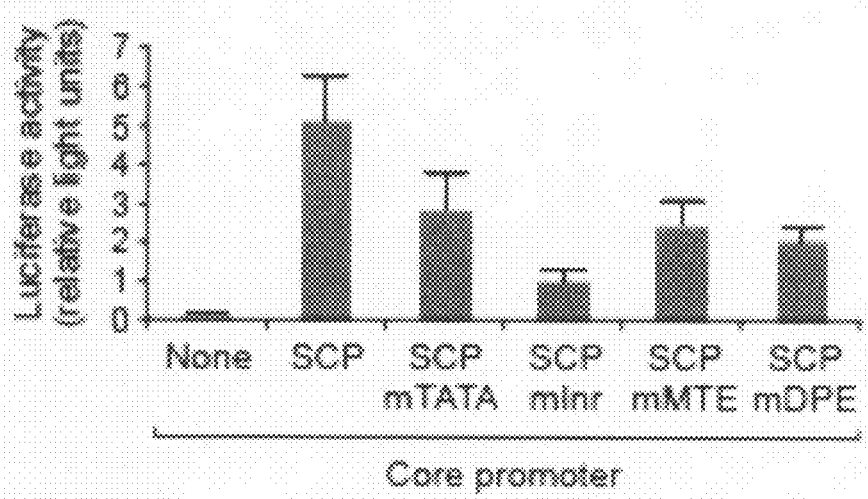
Figure 16C:
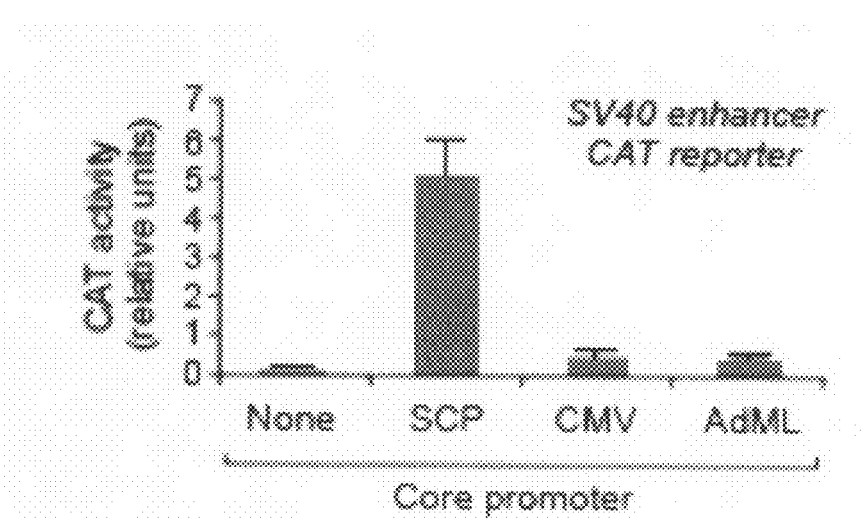
Figure 16D:
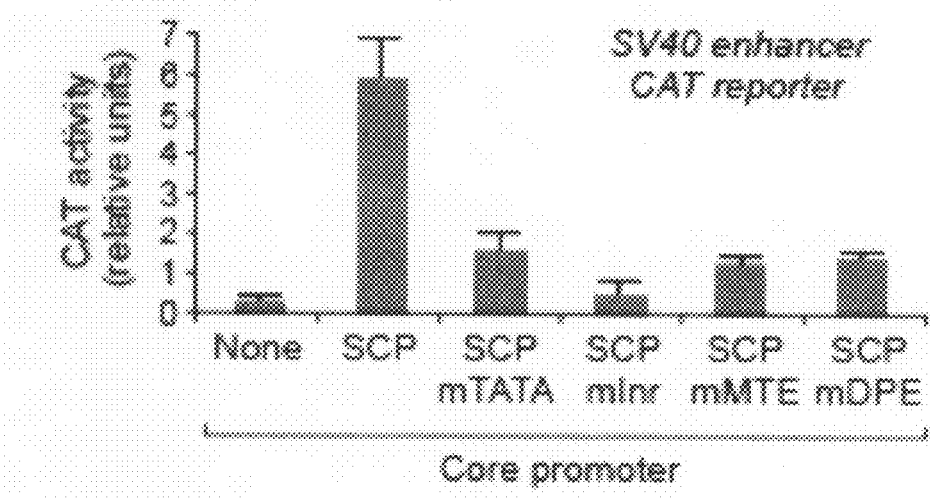

It was important to assess whether the SCP can increase enhancer-driven transcription. To test this, the SCP, CMV, and AdML core promoters were inserted into the pGL3-Enhancer luciferase reporter vector (which contains the SV40 enhancer; Promega, Madison, Wis.), and tested the activities of the resulting constructs by transient transfection analysis (FIG. 16A). The results indicate that the SCP is about threefold more active than the CMV or AdML core promoters with the SV40 enhancer and luciferase reporter. Each of the core promoter motifs was found to contribute to SCP function with the SV40 enhancer (FIG. 16B). To test whether the SCP can enhance transcription in conjunction with a chloramphenicol acetyltransferase (CAT) reporter gene plasmids with the pCAT3-Enhancer vector (which contains the SV40 enhancer; Promega) containing the SCP, CMV, and AdML core promoters were constructed. Transient transfection into HeLa S3 cells revealed that the SCP yields about 10-fold higher levels of CAT activity than the CMV or AdML core promoters (FIG. 16C). In addition, each of the four core promoter motifs (TATA, Inr, MTE, DPE) was found to be important for SCP activity with the SV40 enhancer and CAT reporter (FIG. 16D). Additionally, as shown in FIG. 15, the SCP is about three- to six-fold more active than the CMV or AdML core promoters in CHO cells in a vector containing the SV40 enhancer and a luciferase reporter gene. Thus, the activity of the SCP is not restricted to a specific cell type. Hence, the experiments in FIG. 15 and in FIG. 16A-16D reveal the following: (i) the SCP functions as a potent core promoter in conjunction with the SV40 enhancer; (ii) the SCP can be used to increase the production of two different proteins (luciferase, CAT); and (iii) the SCP functions in both HeLa (human) and CHO (hamster) cells. In addition to its function with mammalian transcription factors, the SCP is also a potent core promoter with insect (*Drosophila*) factors both in vitro and in S2 cultured cells.

EXAMPLE 20

The SCP Directs Accurate Initiation of Transcription In Vivo

Figure 17A:
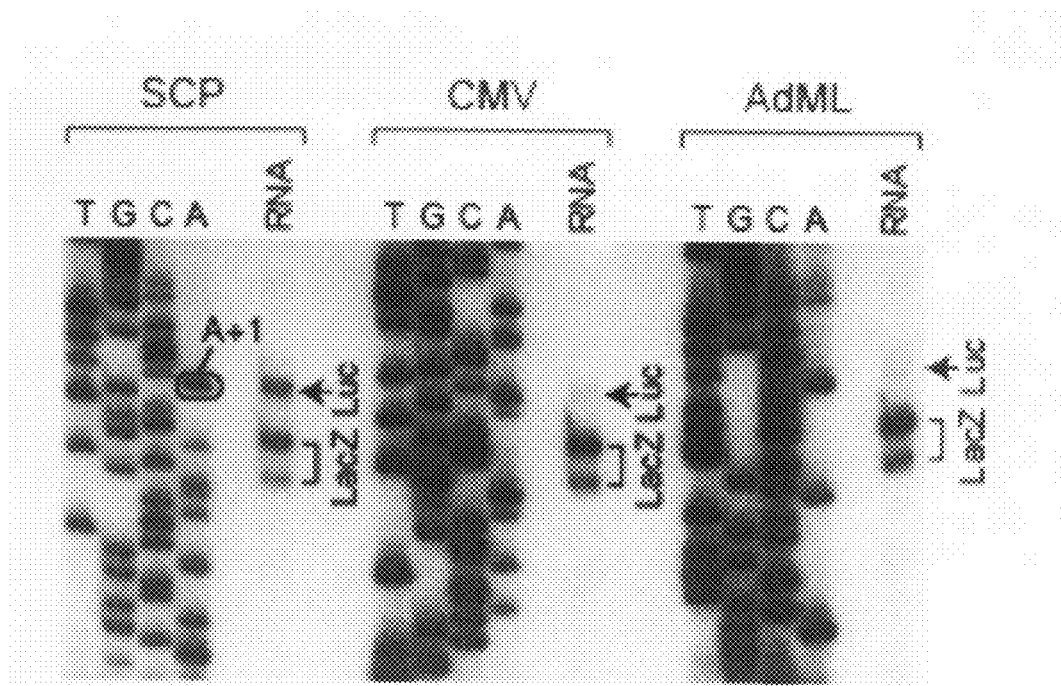
FIGS. 17A-17B show that the SCP mediates robust, accurate initiation of transcription in HeLa S3 cells and that transcription from the SCP initiates from the A+1 in the Inr motif. HeLa S3 cells were transfected with constructs containing the SV40 enhancer linked to the SCP, CMV, or AdML core promoters, along with a β-galactosidase (LacZ) reporter as a control. Total RNA was extracted from cells and subjected to primer extension analysis with luciferase (Luc) and LacZ primers. The SCP yields more transcripts than the CMV or AdML core promoters (FIG. 17A). As both the Luc and LacZ primers were used in the primer extension reactions above, it was not possible to unambiguously determine whether there was any downstream initiation of Luc transcripts. So the experiment was repeated by analyzing the Luc transcripts in the absence of the LacZ primer. This experiment revealed that the Luc transcripts were generated from the SCP initiated at the A+1 in the Inr (FIG. 17B).
Figure 17B:
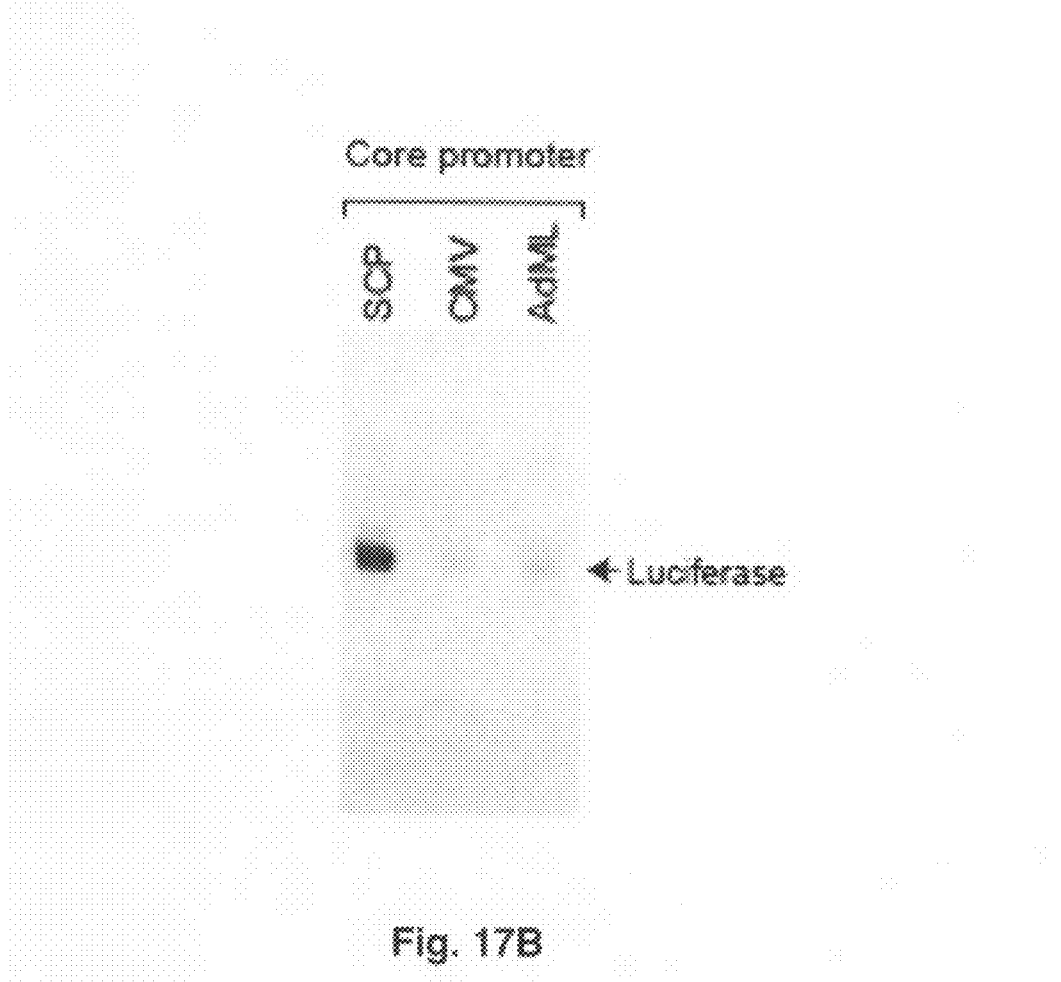

Although the SCP can increase protein production in cells, it was also important to examine whether the SCP directs accurate initiation of transcription from the +1 start site. To this end, HeLa S3 cells was transfected with pGL3-Enhancer constructs containing the SCP, CMV, or AdML core promoters, the RNA was isolated from the cells, and the RNA was subjected to primer extension analysis. As a control for transfection efficiency, the cells were also co-transfected with a β-galactosidase reporter plasmid. As shown in FIG. 17A, the SCP mediates transcription from the A+1 site in the Inr motif. In addition, the amount of RNA produced from the SCP was considerably higher than that from the CMV or AdML core promoters. Because both luciferase (Luc) and LacZ primers were used in the primer extension reactions in FIG. 17A, it was not possible to determine unambiguously whether there was any downstream initiation of Luc transcripts. The Luc transcripts were therefore analyzed in the absence of the LacZ primer. This experiment revealed that the Luc transcripts generated from the SCP initiated at the A+1 in the Inr (FIG. 17B). One can thus conclude that the SCP directs robust and accurate initiation of transcription in vivo.

EXAMPLE 21

New SCPs for Specific Applications

Figure 18B:
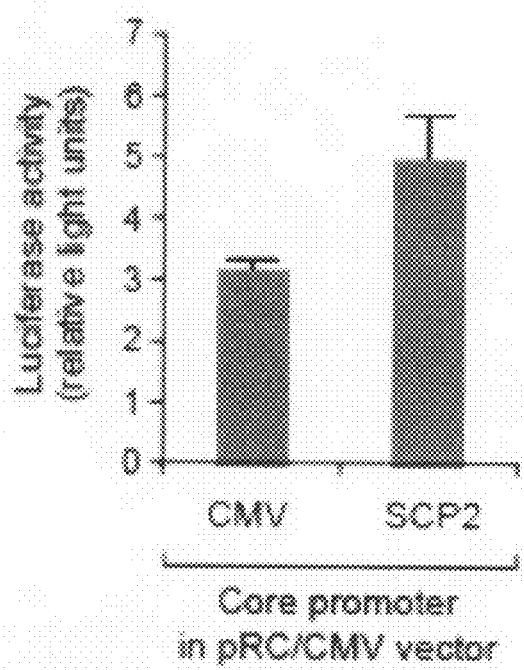

To further explore the range of SCP function the activity of SCP in conjunction with the CMV enhancer was studied. To this end, the pRC/CMV vector (Invitrogen) with a luciferase reporter gene was used. pRC/CMV contains the CMV enhancer and promoter sequences, but lacks CMV core promoter sequences (including the Inr) downstream of −16 relative to the normal +1 CMV start site. The activity of pRC/CMV relative to variants that contain either the SCP or natural CMV core promoter sequences to +45 was compared. These experiments revealed that the replacement of pRC/CMV core promoter sequences with the SCP results in an increase of activity, but also that the natural CMV core promoter (CMV) is more active than the SCP in the context of the CMV enhancer (FIG. 19A). This effect is likely due to the optimization of the function of the CMV core promoter with the CMV enhancer. To see if the activity of the SCP could be further enhanced using the CMV enhancer element a new super core promoter, termed SCP2 (AGGTCTATATAAGCAGAGCTCGTTTAGTGAACCGTCAGATCGC-CTGGAGACGTC GAGCCGAGTGGTTGTGCCTC-CATAGAA, SEQ ID NO: 23) that contains the CMV TATA and Inr along with the Drosophila Tollo MTE and a consensus DPE was constructed. In HeLa S3 cells (FIG. 18A) as well as in CHO cells (FIG. 18B), SCP2 yields higher activity than the natural CMV core promoter in conjunction with the CMV enhancer. Thus, the SCP strategy of using multiple core promoter motifs to increase transcriptional activity can be used to generate new SCPs that function in different contexts.

EXAMPLE 22

Applications of the Super Core Promoter (SCP)

The present invention examines the use of the SCP in the production of erythropoietin (EPO) and tissue plasminogen activator (tPA) in CHO cells. The amount of protein produced with the SCP is compared to that produced with the CMV immediate early core promoter or the core promoter in the pRC/CMV (Invitrogen) vector which is a truncated version of the CMV immediate early core promoter. The cDNAs for human EPO and tPA are known and obtained and their coding regions, with a C-terminal FLAG tag, are cloned into three parallel expression vectors: (1) pRC/CMV; (2) a pRC/CMV derivative in which the core promoter has been replaced by the SCP; and (3) a pRC/CMV derivative in which the core promoter has been replaced by the complete CMV immediate early core promoter.

Whether the SCP can mediate the production of higher levels of recombinant proteins, relative to that obtained with the CMV core promoter constructs, is examined by transient transfection of CHO cells. To assess the amount of each protein that is produced and secreted from the cells, the supernatant of the cell culture is collected and the amount of the recombinant protein is assessed by western blot analysis with antibodies that recognize the FLAG epitope. It is also possible that a several-fold increase in transcription may result in a more modest increase in protein production. However, for proteins such as EPO and tPA, even a modest increase in protein production can have enormous economic consequences.

The following references were cited herein:
1. Smale, S T, (1997) Biochim. Biophys. Acta 1351:73-88.
2. Smale, S T, (2001) Genes Dev. 15:2503-2508.
3. Butler, J E F and Kadonaga, J T, (2002) Genes Dev. 16:2583-2592.
4. Hochheimer, A and Tjian, R, (2003) Genes Dev. 17:1309-1320.
5. Smale and Kadonaga, (2003) Annu. Rev. Biochem. 72:449-479.
6. Goldberg, M L (1979) Ph.D. thesis (Stanford University).
7. Lagrange, et al. (1998) Genes Dev. 12:34-44.
8. Smale, S T and Baltimore, D, (1989) Cell 57:103-113.
9. Kaufmann, J, and Smale, S T, (1994) Genes Dev. 8:821-829.
10. Purnell, et al., (1994) Genes Dev. 8:830-842.
11. Verrijzer, et al. (1994) Science 264:933-941.
12. Chalkley, G E and Verrijzer, C P, (1999) EMBO J. 18:4835-4845.
13. Burke, T W and Kadonaga, J T, (1996) Genes Dev. 10:711-724.
14. Burke, T W and Kadonaga, J T, (1997) Genes Dev. 11:3020-3031.
15. Kutach, A K and Kadonaga, J T, (2000) Mol. Cell. Biol. 20:4754-4764.
16. Shao, et al., (2005) Mol. Cell. Biol. 25:206-219.
17. Chen, Z and Manley, J L, (2003) Mol. Cell. Biol. 23:7350-7362.
18. Willy, et al. (2000) Science 290:982-984
19. Butler, J E F and Kadonaga, J T, (2001) Genes Dev. 15:2515-2519.
20. Ohler, et al (2002) Genome Bio 3: research 0087.1-research 0087.12.
21. Wampler, S. L. et al. (1990) J Biol Chem 265, 21223-21231.
22. Kraus and Kadonaga, (1999) Ligand and cofactor-regulated transcription with chromatin templates. In Nuclear receptors: A practical approach (ed. D. Picard), pp. 167-189. Oxford University Pres, Oxford/New York.
23. Soeller, et al. (1988) Genes & Dev 2:68-81.
24. Dignam, et al. (1983) Nucleic Acids Res. 11:1475-1489.
25. Hawley et al. (1985) J. Biol. Chem. 260:8163-8172.
26. Hawley et al. (1987) J. Biol. Chem. 262: 3452-3461.
27. Kadonaga, J. T. (1990) J. Biol. Chem. 265: 2624-2631.
28. Nishi, et al. (2000) Biochim Biophys Acta 1490:106-108.
29. Sugawara, et al. (2001) Biochim Biophys Acta 1533:277-284.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds, compositions, vectors, cells, etc. described herein are presently representative of preferred embodiments, are exemplary, and are not intended as limitations on the scope of the invention. Changes therein and other uses will occur to those skilled in the art which are encompassed within the spirit of the invention as defined by the scope of the claims.

SEQUENCE LISTING

```
<160> NUMBER OF SEQ ID NOS: 61

<210> SEQ ID NO 1
<211> LENGTH: 12
<212> TYPE: DNA
<213> ORGANISM: artificial sequence
<220> FEATURE:
<223> OTHER INFORMATION: Consensus Sequence in the Motif 10 sequence of
      Drosophila core promoters

<400> SEQUENCE: 1
csarcssaac gs                                                          12

<210> SEQ ID NO 2
<211> LENGTH: 10
<212> TYPE: DNA
<213> ORGANISM: artificial sequence
<220> FEATURE:
<223> OTHER INFORMATION: Nucleotide sequence of the Motif ten element in
      Drosophila core promoters

<400> SEQUENCE: 2 csarcssaac                                                             10

<210> SEQ ID NO 3
<211> LENGTH: 7
<212> TYPE: DNA
<213> ORGANISM: artificial sequence
<220> FEATURE:
<223> OTHER INFORMATION: The consensus nucleotide sequence in TFIIB
      recognition element of Drosophila

<400> SEQUENCE: 3 ssrcgcc                                                                 7

<210> SEQ ID NO 4
<211> LENGTH: 6
<212> TYPE: DNA
<213> ORGANISM: artificial sequence
<220> FEATURE:
<223> OTHER INFORMATION: Nucleotide sequence of Initiator element in
      Drosophila

<400> SEQUENCE: 4 tcakty                                                                  6

<210> SEQ ID NO 5
<211> LENGTH: 8
<212> TYPE: DNA
<213> ORGANISM: artificial sequence
<220> FEATURE:
<223> OTHER INFORMATION: Nucleotide sequence of TATA box in Drosophila

<400> SEQUENCE: 5 tatawaar                                                                8

<210> SEQ ID NO 6
```

```
<211> LENGTH: 6
<212> TYPE: DNA
<213> ORGANISM: artificial sequence
<220> FEATURE:
<223> OTHER INFORMATION: Nucleotide sequence of downstream promoter
      element in Drosophila

<400> SEQUENCE: 6 rgwyvt                                                              6

<210> SEQ ID NO 7
<211> LENGTH: 11
<212> TYPE: DNA
<213> ORGANISM: artificial sequence
<220> FEATURE:
<223> OTHER INFORMATION: Optimized Motif 10 element from the Drosophila
      Tollo core promoter

<400> SEQUENCE: 7
tcgagccgag c                                                       11

<210> SEQ ID NO 8
<211> LENGTH: 81
<212> TYPE: DNA
<213> ORGANISM: artificial sequence
<220> FEATURE:
<223> OTHER INFORMATION: Nucleotide sequence of the super core promoter
      (SCP1)

<400> SEQUENCE: 8
gtacttatat aagggggtgg gggcgcgttc gtcctcagtc gcgatcgaac              50
actcgagccg agcagacgtg cctacggacc g                                 81

<210> SEQ ID NO 9
<211> LENGTH: 24
<212> TYPE: DNA
<213> ORGANISM: artificial sequence
<220> FEATURE:
<223> OTHER INFORMATION: M13 reverse sequencing primer to amplify
      transcripts from pUC 119 constructs

<400> SEQUENCE: 9
agcggataac aatttcacac agga                                         24

<210> SEQ ID NO 10
<211> LENGTH: 10
<212> TYPE: DNA
<213> ORGANISM: artificial sequence
<220> FEATURE:
<223> OTHER INFORMATION: Tandemly repeated nucleotide sequence in motif
      10

<400> SEQUENCE: 10
aacggaacgg                                                         10

<210> SEQ ID NO 11
<211> LENGTH: 7
<212> TYPE: DNA
<213> ORGANISM: artificial sequence
<220> FEATURE:
<222> LOCATION: 4
<223> OTHER INFORMATION: Inr consensus nucleotide sequence in humans
      where n is any nucleotide at position 4

<400> SEQUENCE: 11 yyanwyy                                                             7
```

<210> SEQ ID NO 12
<211> LENGTH: 4
<212> TYPE: DNA
<213> ORGANISM: artificial sequence
<220> FEATURE:
<223> OTHER INFORMATION: Nucleotide sequence of the mutation in the +30
      to +33 region of E74B and Doc core promoters

<400> SEQUENCE: 12 cata                                                                      4

<210> SEQ ID NO 13
<211> LENGTH: 6
<212> TYPE: DNA
<213> ORGANISM: artificial sequence
<220> FEATURE:
<223> OTHER INFORMATION: Nucleotide sequence of the mutations in the Inr
      sequence

<400> SEQUENCE: 13 gtgaca                                                                    6

<210> SEQ ID NO 14
<211> LENGTH: 8
<212> TYPE: DNA
<213> ORGANISM: artificial sequence
<220> FEATURE:
<223> OTHER INFORMATION: Nucleotide sequence of the hbP2 TATA-box

<400> SEQUENCE: 14 tatataaa                                                                  8

<210> SEQ ID NO 15
<211> LENGTH: 7
<212> TYPE: DNA
<213> ORGANISM: artificial sequence
<220> FEATURE:
<223> OTHER INFORMATION: Nucleotide sequence of the mutations in the
      hbP2 TATA-box sequence

<400> SEQUENCE: 15 acgtcgt                                                                   7

<210> SEQ ID NO 16
<211> LENGTH: 5
<212> TYPE: DNA
<213> ORGANISM: artificial sequence
<220> FEATURE:
<223> OTHER INFORMATION: Nucleotide sequence of the m18-22 mutation in
      TATA-Inr and Inr constructs

<400> SEQUENCE: 16 atcca                                                                     5

<210> SEQ ID NO 17
<211> LENGTH: 30
<212> TYPE: DNA
<213> ORGANISM: artificial sequence
<220> FEATURE:
<223> OTHER INFORMATION: CYLuc2 primer strand for amplification of
      transcripts from pGL3-Basic constructs

<400> SEQUENCE: 17
agtaccggaa tgccaagctt aattagatcg                                         30

<210> SEQ ID NO 18
<211> LENGTH: 24
<212> TYPE: DNA

```
<213> ORGANISM: artificial sequence
<220> FEATURE:
<223> OTHER INFORMATION: TGluc3 primer strand for amplification of
      transcripts from pGL3-Enhancer constructs

<400> SEQUENCE: 18
tcttccagcg gatagaatgg cgcc                                          24

<210> SEQ ID NO 19
<211> LENGTH: 24
<212> TYPE: DNA
<213> ORGANISM: artificial sequence
<220> FEATURE:
<223> OTHER INFORMATION: CAT-PE primer strand for amplification of
      transcripts from pCAT3-Enhancer constructs

<400> SEQUENCE: 19
acttctgcag ttaagcggcc gcaa                                          24

<210> SEQ ID NO 20
<211> LENGTH: 26
<212> TYPE: DNA
<213> ORGANISM: artificial sequence
<220> FEATURE:
<223> OTHER INFORMATION: Lac-Z specific primer strand

<400> SEQUENCE: 20
tcccagtcac gacgttgtaa aacgac                                        26

<210> SEQ ID NO 21
<211> LENGTH: 81
<212> TYPE: DNA
<213> ORGANISM: artificial sequence
<220> FEATURE:
<223> OTHER INFORMATION: Nucleotide Sequence of the adenovirus major
      late core promoter

<400> SEQUENCE: 21
aggtctatat aagcagagct cgtttagtga accgtcagat cgcctggaga              50
cgccatccac gctgttttga cctccataga a                                  81

<210> SEQ ID NO 22
<211> LENGTH: 81
<212> TYPE: DNA
<213> ORGANISM: artificial sequence
<220> FEATURE:
<223> OTHER INFORMATION: Nucleotide Sequence of the cytomegalovirus
      immediate early (IE1) core promoter

<400> SEQUENCE: 22
ggggctataa aaggggtgg gggcgcgttc gtcctcactc tcttccgcat               50
cgctgtctgc gagggccagc tgttggggtg a                                  81

<210> SEQ ID NO 23
<211> LENGTH: 81
<212> TYPE: DNA
<213> ORGANISM: artificial sequence
<220> FEATURE:
<223> OTHER INFORMATION: Nucleotide Sequence of the super core promoter
      (SCP2) with the CMV enhancer element

<400> SEQUENCE: 23
aggtctatat aagcagagct cgtttagtga accgtcagat cgcctggaga              50
cgtcgagccg agtggttgtg cctccataga a                                  81
```

-continued

<210> SEQ ID NO 24
<211> LENGTH: 45
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 24
ttttcattcg tctcttgaat tccgaacgca acggttcgcc ttcgc          45

<210> SEQ ID NO 25
<211> LENGTH: 45
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 25
gtttcagtcg agcgacgcaa ctcgaacgca acggtacatg agtgg          45

<210> SEQ ID NO 26
<211> LENGTH: 45
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 26
ggctcagttc accgctgatt ctcgaaccaa acggaagcaa aatga          45

<210> SEQ ID NO 27
<211> LENGTH: 45
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 27
atgtcatttg tcaatcacag tgcgagcgca acggttgtcc gaacc          45

<210> SEQ ID NO 28
<211> LENGTH: 45
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 28
tcgtcagttg agtgttaagt accgagcgga gcggacatat ggggt          45

<210> SEQ ID NO 29
<211> LENGTH: 45
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 29
atttcattcc ctctgcgcac ttcgaaccga tcgctcgtat cgctc          45

<210> SEQ ID NO 30
<211> LENGTH: 45

```
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 30
cgatcagttt ttgagttgac ttcgagccga gcggacgcgc gtttg            45

<210> SEQ ID NO 31
<211> LENGTH: 45
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 31
atttcagtcg ggaaattttg cacaagccaa gcgcacgcgg cagcg            45

<210> SEQ ID NO 32
<211> LENGTH: 45
<212> TYPE: DNA
<213> ORGANISM: artificial sequence
<220> FEATURE:
<223> OTHER INFORMATION: Putative core promoter sequence with the motif
      10 sequence as in the Drosophila genome

<400> SEQUENCE: 32
agctcatttc gacgcgcact ttcaagcgga gcggttcgtt cgttt            45

<210> SEQ ID NO 33
<211> LENGTH: 42
<212> TYPE: DNA
<213> ORGANISM: artificial sequence
<220> FEATURE:
<223> OTHER INFORMATION: CG4427 core promoter sequence containing the
      Inr, motif 10 and DPE sequence

<400> SEQUENCE: 33
tcattcgtct cttgaattcc gaacgcaacg gttcgccttc gc               42

<210> SEQ ID NO 34
<211> LENGTH: 42
<212> TYPE: DNA
<213> ORGANISM: artificial sequence
<220> FEATURE:
<223> OTHER INFORMATION: CG4427 core promoter sequence with the m11-13
      mutation

<400> SEQUENCE: 34
tcattcgtct ctcccattcc gaacgcaacg gttcgccttc gc               42

<210> SEQ ID NO 35
<211> LENGTH: 42
<212> TYPE: DNA
<213> ORGANISM: artificial sequence
<220> FEATURE:
<223> OTHER INFORMATION: CG4427 core promoter sequence with the m14-16
      mutation

<400> SEQUENCE: 35
tcattcgtct cttgaccccc gaacgcaacg gttcgccttc gc               42

<210> SEQ ID NO 36
<211> LENGTH: 42
<212> TYPE: DNA
<213> ORGANISM: artificial sequence
```

-continued

```
<220> FEATURE:
<223> OTHER INFORMATION: CG4427 core promoter sequence with the m17-19
      mutation

<400> SEQUENCE: 36
tcattcgtct cttgaattaa taacgcaacg gttcgccttc gc                          42

<210> SEQ ID NO 37
<211> LENGTH: 42
<212> TYPE: DNA
<213> ORGANISM: artificial sequence
<220> FEATURE:
<223> OTHER INFORMATION: CG4427 core promoter sequence with the m20-22
      mutation

<400> SEQUENCE: 37
tcattcgtct cttgaattcc gccagcaacg gttcgccttc gc                          42

<210> SEQ ID NO 38
<211> LENGTH: 42
<212> TYPE: DNA
<213> ORGANISM: artificial sequence
<220> FEATURE:
<223> OTHER INFORMATION: CG4427 core promoter sequence with the m23-25
      mutation

<400> SEQUENCE: 38
tcattcgtct cttgaattcc gaactacacg gttcgccttc gc                          42

<210> SEQ ID NO 39
<211> LENGTH: 42
<212> TYPE: DNA
<213> ORGANISM: artificial sequence
<220> FEATURE:
<223> OTHER INFORMATION: CG4427 core promoter sequence with the m26-28
      mutation

<400> SEQUENCE: 39
tcattcgtct cttgaattcc gaacgcacat gttcgccttc gc                          42

<210> SEQ ID NO 40
<211> LENGTH: 42
<212> TYPE: DNA
<213> ORGANISM: artificial sequence
<220> FEATURE:
<223> OTHER INFORMATION: CG4427 core promoter sequence with the m29-31
      mutation

<400> SEQUENCE: 40
tcattcgtct cttgaattcc gaacgcaacg ccccgccttc gc                          42

<210> SEQ ID NO 41
<211> LENGTH: 42
<212> TYPE: DNA
<213> ORGANISM: artificial sequence
<220> FEATURE:
<223> OTHER INFORMATION: CG4427 core promoter sequence with the m32-34
      mutation

<400> SEQUENCE: 41
tcattcgtct cttgaattcc gaacgcaacg gttacacttc gc                          42

<210> SEQ ID NO 42
<211> LENGTH: 42
<212> TYPE: DNA
<213> ORGANISM: artificial sequence
<220> FEATURE:
<223> OTHER INFORMATION: CG4427 core promoter sequence with the m35-37
```

-continued

```
                                                              mutation

<400> SEQUENCE: 42
tcattcgtct cttgaattcc gaacgcaacg gttcgcaccc gc                        42

<210> SEQ ID NO 43
<211> LENGTH: 39
<212> TYPE: DNA
<213> ORGANISM: artificial sequence
<220> FEATURE:
<223> OTHER INFORMATION: Tollo core promoter sequence containing the
      Inr, motif 10 and DPE sequence

<400> SEQUENCE: 43 tcagttttg agttgacttc gagccgagcg gacgcgcgt                             39

<210> SEQ ID NO 44
<211> LENGTH: 39
<212> TYPE: DNA
<213> ORGANISM: artificial sequence
<220> FEATURE:
<223> OTHER INFORMATION: Tollo core promoter sequence with the m18-19
      mutation

<400> SEQUENCE: 44 tcagttttg agttgactta tagccgagcg gacgcgcgt                             39

<210> SEQ ID NO 45
<211> LENGTH: 39
<212> TYPE: DNA
<213> ORGANISM: artificial sequence
<220> FEATURE:
<223> OTHER INFORMATION: Tollo core promoter sequence containing the
      Inr, motif 10 and DPE sequence

<400> SEQUENCE: 45 tcagttttg agttgactta tccccgagcg gacgcgcgt                             39

<210> SEQ ID NO 46
<211> LENGTH: 39
<212> TYPE: DNA
<213> ORGANISM: artificial sequence
<220> FEATURE:
<223> OTHER INFORMATION: Tollo core promoter sequence with the m18-22
      mutation

<400> SEQUENCE: 46 tcagttttg agttgactta tccacgagcg gacgcgcgt                             39

<210> SEQ ID NO 47
<211> LENGTH: 39
<212> TYPE: DNA
<213> ORGANISM: artificial sequence
<220> FEATURE:
<223> OTHER INFORMATION: Tollo core promoter sequence with the m18-23
      mutation mutation

<400> SEQUENCE: 47 tcagttttg agttgactta tccatgagcg gacgcgcgt                             39

<210> SEQ ID NO 48
<211> LENGTH: 39
<212> TYPE: DNA
<213> ORGANISM: artificial sequence
<220> FEATURE:
<223> OTHER INFORMATION: Tollo core promoter sequence with the m18-24
      mutation
```

-continued

```
<400> SEQUENCE: 48 tcagttttttg agttgactta tccattagcg dacgcgcgt                            39

<210> SEQ ID NO 49
<211> LENGTH: 39
<212> TYPE: DNA
<213> ORGANISM: artificial sequence
<220> FEATURE:
<223> OTHER INFORMATION: Tollo core promoter sequence with the m18-28
      mutation

<400> SEQUENCE: 49 tcagttttttg agttgactta tccatcccaa dacgcgcgt                            39

<210> SEQ ID NO 50
<211> LENGTH: 42
<212> TYPE: DNA
<213> ORGANISM: artificial sequence
<220> FEATURE:
<223> OTHER INFORMATION: Tollo core promoter sequence containing the
      Inr, motif 10 and DPE sequence

<400> SEQUENCE: 50 tcagttttttg agttgacttc gagccgagcg dacgcgcgtt tg                        42

<210> SEQ ID NO 51
<211> LENGTH: 42
<212> TYPE: DNA
<213> ORGANISM: artificial sequence
<220> FEATURE:
<223> OTHER INFORMATION: Tollo core promoter sequence with the m18-22
      mutation

<400> SEQUENCE: 51 tcagttttttg agttgactta tccacgagcg dacgcgcgtt tg                        42

<210> SEQ ID NO 52
<211> LENGTH: 42
<212> TYPE: DNA
<213> ORGANISM: artificial sequence
<220> FEATURE:
<223> OTHER INFORMATION: Tollo core promoter sequence with the m30-33
      mutation

<400> SEQUENCE: 52 tcagttttttg agttgacttc gagccgagcg gcatagcgtt tg                        42

<210> SEQ ID NO 53
<211> LENGTH: 42
<212> TYPE: DNA
<213> ORGANISM: artificial sequence
<220> FEATURE:
<223> OTHER INFORMATION: Tollo core promoter sequence with the
      m18-22/30-33 mutations

<400> SEQUENCE: 53 tcagttttttg agttgactta tccacgagcg gcatagcgtt tg                        42

<210> SEQ ID NO 54
<211> LENGTH: 41
<212> TYPE: DNA
<213> ORGANISM: artificial sequence
<220> FEATURE:
<223> OTHER INFORMATION: Tollo core promoter sequence with the m30-33
      m18-22/30-33 and where the distance between the Inr and the MTE is
      decreased by one nucleotide

<400> SEQUENCE: 54
```

-continued

```
tcagttttg agttgactcg agccgagcgg catagcgttt g                41
```

<210> SEQ ID NO 55
<211> LENGTH: 39
<212> TYPE: DNA
<213> ORGANISM: artificial sequence
<220> FEATURE:
<223> OTHER INFORMATION: Tollo core promoter sequence with the m30-33
      mutation where the distance between the Inr and the MTE is
      decreased by three nucleotides

<400> SEQUENCE: 55

```
tcagttttg agttgtcgag ccgagcggca tagcgtttg                  39
```

<210> SEQ ID NO 56
<211> LENGTH: 43
<212> TYPE: DNA
<213> ORGANISM: artificial sequence
<220> FEATURE:
<223> OTHER INFORMATION: Tollo core promoter sequence with the m30-33
      mutation where the distance between the the Inr and the MTE is
      increased by one nucleotide

<400> SEQUENCE: 56

```
tcagttttg agttgactat cgagccgagc ggcatagcgt ttg             43
```

<210> SEQ ID NO 57
<211> LENGTH: 45
<212> TYPE: DNA
<213> ORGANISM: artificial sequence
<220> FEATURE:
<223> OTHER INFORMATION: Tollo core promoter sequence with the m30-33
      mutation where the distance between the the Inr and the MTE is
      increased by three nucleotides

<400> SEQUENCE: 57

```
tcagttttg agttgactaa atcgagccga gcggcatagc gtttg           45
```

<210> SEQ ID NO 58
<211> LENGTH: 41
<212> TYPE: DNA
<213> ORGANISM: artificial sequence
<220> FEATURE:
<223> OTHER INFORMATION: Nucleotide sequence of the MTE dependent
      promotor of the human sterol C5 desaturase-like (SC5DL) gene

<400> SEQUENCE: 58

```
acagtttgca gagcagtggc gtgcggagcg gcggcggacc a              41
```

<210> SEQ ID NO 59
<211> LENGTH: 81
<212> TYPE: DNA
<213> ORGANISM: artificial sequence
<220> FEATURE:
<223> OTHER INFORMATION: Nucleotide sequence of the super core promoter
      SCP1 variant (SCP-T1)

<400> SEQUENCE: 59

```
gtacttatat aagggggtgg gggcgcgttc gtcttcagtt ttttttcaac      50
actcgagccg agcagacgtg cctacggacc g                         81
```

<210> SEQ ID NO 60
<211> LENGTH: 81
<212> TYPE: DNA
<213> ORGANISM: artificial sequence
<220> FEATURE:
<223> OTHER INFORMATION: Nucleotide sequence of the super core promoter

```
            SCP1 variant (SCP-T2)

<400> SEQUENCE: 60
gtacttatat aaggggtgg gggcgcgttc gtcttcagtt tcgtttcaac              50
actcgagccg agcagacgtg cctacggacc g                                81

<210> SEQ ID NO 61
<211> LENGTH: 81
<212> TYPE: DNA
<213> ORGANISM: artificial sequence
<220> FEATURE:
<223> OTHER INFORMATION: Nucleotide Sequence of the super core promoter
      (SCP3) with the CMV enhancer element

<400> SEQUENCE: 61
aggtctatat aagcagagct cgtttagtga accgtcagtc cgcctggaga              50
cctcgagccg agtggtcgtg cctccataga a                                 81
```

What is claimed is:

1. A synthetic core promoter element, comprising:
a nucleic acid sequence consisting of a consensus sequence shown in SEQ ID NO: 2.

2. A core promoter construct, comprising:
a nucleic acid sequence of a core promoter initiator element (Inr); and a nucleic acid sequence of a core promoter motif ten element (MTE) as shown in SEQ ID NQ:2 operably positioned therewith.

3. The core promoter construct of claim 2, further comprising:
a nucleic acid sequence linking the Inr and the MTE, said nucleic acid sequence having a non-negative effect on core promoter function.

4. The core promoter construct of claim 3, wherein said linking nucleic acid sequence comprises another core promoter sequence.

5. The core promoter construct of claim 4, wherein said linking nucleic acid sequence is a *Drosophila* G element core promoter sequence.

6. The core promoter construct of claim 2, wherein said Inr sequence is derived from a consensus sequence shown in SEQ ID NO: 4 or derived from the CMV Inr sequence.

7. The core promoter construct of claim 2, further comprising:
one or both of a nucleic acid sequence of a TATA box or a nucleic acid sequence of a downstream promoter element (DPE).

8. The core promoter construct of claim 7, further comprising:
nucleic acid sequences linking lnr, MTE, TATA box and DPE in an operable position within the construct, said nucleic acid sequences having a non-negative effect on core promoter function.

9. The core promoter construct of claim 8, wherein said linking nucleic acid sequences comprise other core promoter sequences or a consensus of sequences found in the same relative positions to the transcription start site in a metazoan core promoter.

10. The core promoter construct of claim 9, wherein said linking nucleic acid sequences comprise one or more sequences from CMV core promoter, AdML core promoter, *Drosophila* Kruppel factor (Kr) core promoter, *Drosophila* Tollo core promoter (Tollo), or *Drosophila* G element (G) core promoter.

11. The core promoter construct of claim 10 having a nucleic acid sequence shown in SEQ ID NO: 8, 23, 59, 60, or 61.

12. The core promoter construct of claim 7, wherein said TATA box sequence is derived from a consensus sequence shown in SEQ ID NO: 5 or derived from the CMV TATA sequence.

13. The core promoter construct of claim 7, wherein said DPE sequence is derived from a consensus sequence shown in SEQ ID NO: 6.

14. The core promoter construct of claim 2, further comprising:
a nucleic acid sequence of a TATA box; a nucleic acid sequence of a downstream promoter element (DPE); and other nucleic acid sequences linking lnr, MTE, TATA box and DPE in a synergistically operable position within the construct, said other nucleic acid sequences having a non-negative effect on core promoter function.

15. An expression vector comprising the core promoter construct of claim 2.

16. The expression vector of claim 15, further comprising:
a nucleic acid encoding a therapeutic protein, a reporter protein, a transcription enhancer element or a combination thereof operably linked to the promoter.

17. The expression vector of claim 16, wherein said therapeutic protein is erythropoietin, tissue plasminogen activator or an antibody.

18. The expression vector of claim 16, wherein said reporter protein is .beta.-galactosidase, luciferase, chloramphenicol acetyl transferase or a green fluorescent protein.

19. The expression vector of claim 16, wherein said enhancer element is an SV40 enhancer element or a CMV enhancer element.

20. A metazoan host cell comprising and expressing the expression vector of claim 15.

21. The metazoan host cell of claim 20, wherein said metazoan cell is a HeLa cell, a CHO cell, a BHK cell, a HEK-293 cell, or a *Drosophila* S2 cell.

22. A kit comprising the core promoter construct of claim 2.

23. The kit of claim 22, further comprising:
an expression vector comprising said core promoter construct and a metazoan host cell suitable to express said expression vector.

24. A method for increasing production of a protein in a metazoan cell, comprising:
introducing into a metazoan host cell an expression vector comprising the core promoter construct of claim 2 and a nucleic acid sequence encoding a protein; culturing the metazoan host cell under conditions suitable to express said protein; and isolating said expressed protein, wherein the core promoter increases expression of the nucleic acid sequence encoding the protein thereby increasing production thereof.

25. The method of claim 24, wherein said nucleic acid sequence encodes a therapeutic protein, a reporter protein or a combination thereof.

26. A method for increasing expression of genes in a metazoan animal, comprising:
introducing an expression vector comprising the core promoter construct of claim 2 and a nucleic acid sequence comprising one or more genes into a metazoan animal such that a transgenic metazoan animal is formed, wherein the core promoter increases expression of the gene(s) comprised within the expression vector therein.

27. The method of claim 26, wherein the metazoan animal is Drosophila, a leech, a mouse, or a human.

28. A Super Core Promoter having a sequence shown in SEQ ID NO: 8, 23, 59, 60, or 61.

29. A method of designing an optimized core promoter to increase transcription of a gene, comprising:
selecting a nucleic acid sequence for a core promoter initiator element (Inr) and for a core promoter motif ten element (MTE) as shown in SEQ ID NO:2; selecting a nucleic acid sequence from sequences comprising one or more other core promoters; comparing a level of transcriptional activity of Inr operably linked to MTE with a level of transcriptional activity of operably linked Inr, MTE and one or more of said other core promoter elements; wherein a combination of Inr, MTE and said one or more other core promoter elements having the highest level of transcriptional activity is the optimized core promoter.

30. The method of claim 29, wherein said Inr sequence is derived from a consensus sequence shown in SEQ ID NO: 4 or derived from the CMV Inr sequence.

31. The method of claim 29, wherein said one or more other core promoter sequences comprise a TATA box sequence or a DPE sequence or a Drosophila G element core promoter sequence, a Drosophila Tollo core promoter sequence, a Drosophila Kruppel core sequence, a CMV core promoter sequence, or an AdML core promoter sequence or a combination thereof.

32. The method of claim 31, wherein said TATA box sequence is derived from a consensus sequence shown in SEQ ID NO: 5 or derived from the CMV TATA sequence.

33. The method of claim 31, wherein said DPE sequence is derived from a consensus sequence shown in SEQ ID NO: 6.

34. The method of claim 27, wherein said optimized core promoter has a nucleic acid sequence shown in SEQ ID NO: 8, 23, 59, 60, or 61.

* * * * *